(12) United States Patent
Konno et al.

(10) Patent No.: US 11,534,121 B2
(45) Date of Patent: Dec. 27, 2022

(54) INFORMATION PROCESSING APPARATUS, INFORMATION PROCESSING METHOD, AND INFORMATION PROCESSING PROGRAM

(71) Applicant: FUJIFILM CORPORATION, Tokyo (JP)

(72) Inventors: Shinichiro Konno, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 105 days.

(21) Appl. No.: 17/213,236

(22) Filed: Mar. 26, 2021

(65) Prior Publication Data
US 2021/0298702 A1    Sep. 30, 2021

(30) Foreign Application Priority Data

Mar. 31, 2020   (JP) .............................. JP2020-065266

(51) Int. Cl.
*A61B 6/00*   (2006.01)
*A61B 6/04*   (2006.01)

(52) U.S. Cl.
CPC .......... *A61B 6/4411* (2013.01); *A61B 6/0414* (2013.01); *A61B 6/502* (2013.01); *A61B 6/547* (2013.01)

(58) Field of Classification Search
CPC ....... A61B 6/4411; A61B 6/547; A61B 6/502; A61B 6/0414; A61B 6/4233; A61B 6/469; A61B 6/5217; H04N 5/23229; G06K 9/3233; A61N 5/1049
See application file for complete search history.

(56) References Cited

U.S. PATENT DOCUMENTS

2019/0046135 A1*   2/2019   Hattori ................... G16H 50/30

FOREIGN PATENT DOCUMENTS

JP        2017-225635 A      12/2017

* cited by examiner

*Primary Examiner* — Don K Wong
(74) *Attorney, Agent, or Firm* — Solaris Intellectual Property Group, PLLC

(57) ABSTRACT

A CPU acquires a distance image which indicates a distance to an imaging target and is captured by a TOF camera using, as an imaging region, a region including at least a portion of a region in which an attachable and detachable member is attached to a mammography apparatus. Further, the CPU acquires reference distance information related to a reference value of a distance between the attachable and detachable member and the TOF camera in a state in which the attachable and detachable member is attached to the mammography apparatus. Furthermore, the CPU determines whether or not the attachable and detachable member is attached to the mammography apparatus on the basis of the distance image and the reference distance information.

11 Claims, 16 Drawing Sheets

INFORMATION PROCESSING APPARATUS, INFORMATION PROCESSING METHOD, AND INFORMATION PROCESSING PROGRAM

CROSS-REFERENCE TO RELATED APPLICATIONS

The present application claims priority under 35 U.S.C. § 119 to Japanese Patent Application No. 2020-065266, filed on Mar. 31, 2020. The above application is hereby expressly incorporated by reference, in its entirety, into the present application.

BACKGROUND

1. Technical Field

The present disclosure relates to an information processing apparatus, an information processing method, and an information processing program.

2. Description of the Related Art

It is known that a radiographic image is captured in a state in which an attachable and detachable member is attached to a radiography apparatus. Therefore, a technique is known which performs determination related to the attachable and detachable member attached to the radiography apparatus. For example, JP2017-225635A discloses a technique that identifies the type of a compression plate which is an example of an attachable and detachable member attached to a mammography apparatus which is an example of a radiography apparatus. In the technique disclosed in JP2017-225635A, the compression plate that compresses the breast is provided with identification information for identifying the type of the compression plate, and an identification sensor provided in a mammography apparatus main body reads the identification information to Identify the type of the compression plate attached to the mammography apparatus.

SUMMARY

However, for example, in a case in which the types of detachable members attached to the radiography apparatus increases, it may be difficult to sufficiently respond to the case, or the size of an apparatus for performing determination related to the attachable and detachable member may increase.

The present disclosure has been made in view of the above-mentioned problems, and an object of the present disclosure is to provide an information processing apparatus, an information processing method, and information processing program that can perform determination related to an attachable and detachable member attached to a radiography apparatus with a simple configuration.

In order to achieve the above object, according to a first aspect of the present disclosure, there is provided an information processing apparatus comprising: at least one processor; and a memory that stores commands executable by the processor. The processor acquires a distance image which indicates a distance to an imaging target and is captured by an imaging device using, as an imaging region, a region including at least a portion of a region in which an attachable and detachable member is attached to a radiography apparatus, acquires reference distance information related to a reference value of a distance between the attachable and detachable member and the imaging device in a state in which the attachable and detachable member is attached to the radiography apparatus, and determines whether or not the attachable and detachable member is attached to the radiography apparatus on the basis of the distance image and the reference distance information.

According to a second aspect of the present disclosure, in the information processing apparatus according to the first aspect, a plurality of types of the attachable and detachable members may be provided, and the processor may determine the type of the attachable and detachable member on the basis of the distance image and the reference distance information.

According to a third aspect of the present disclosure, in the information processing apparatus according to the second aspect, in each type of the attachable and detachable member, at least one of a position where the attachable and detachable member is attached to the radiography apparatus or the distance between the attachable and detachable member and the imaging device in a state in which the attachable and detachable member is attached to the radiography apparatus may be different.

According to a fourth aspect of the present disclosure, in the information processing apparatus according to the first aspect, the radiography apparatus may be a mammography apparatus that captures an image of a breast of a subject, and the attachable and detachable member may be at least one of a compression member that compresses the breast, a protective member that protects the subject from radiation, a magnification imaging table, or a biopsy unit.

According to a fifth aspect of the present disclosure, in the information processing apparatus according to the first aspect, the radiography apparatus may be a mammography apparatus that captures an image of a breast of a subject. The attachable and detachable member may include at least a plurality of types of compression members that compress the breast. The processor may determine the type of the compression member attached to the radiography apparatus on the basis of the distance image and the reference distance information.

According to a sixth aspect of the present disclosure, in the information processing apparatus according to the fifth aspect, the plurality of types of compression members may be provided with marks having different distances from the imaging device for each type.

According to a seventh aspect of the present disclosure, in the information processing apparatus according to the fifth aspect, the plurality of types of compression members may be provided with convex or concave marks having different shapes for each type.

According to an eighth aspect of the present disclosure, in the information processing apparatus according to the first aspect, the reference distance information may be a reference distance map indicating the distance between the imaging device and the attachable and detachable member attached to the radiography apparatus.

According to a ninth aspect of the present disclosure, in the information processing apparatus according to the first aspect, the imaging device may capture the distance image using a time-of-flight (TOF) method.

Further, in order to achieve the above object, according to a tenth aspect of the present disclosure, there is provided an information processing method execute by a computer, the method comprising: acquiring a distance image which indicates a distance to an imaging target and is captured by an imaging device using, as an imaging region, a region including at least a portion of a region in which an attachable and detachable member is attached to a radiography apparatus; acquiring reference distance information related to a reference value of a distance between the attachable and detachable member and the imaging device in a state in which the attachable and detachable member is attached to the radiography apparatus; and determining whether or not the attachable and detachable member is attached to the radiography apparatus on the basis of the distance image and the reference distance information.

Further, in order to achieve the above object, according to an eleventh aspect of the present disclosure, there is provided a non-transitory computer-readable storage medium storing an information processing program that causes a computer to perform a process comprising: acquiring a distance image which indicates a distance to an imaging target and is captured by an imaging device using, as an imaging region, a region including at least a portion of a region in which an attachable and detachable member is attached to a radiography apparatus; acquiring reference distance information related to a reference value of a distance between the attachable and detachable member and the imaging device in a state in which the attachable and detachable member is attached to the radiography apparatus; and determining whether or not the attachable and detachable member is attached to the radiography apparatus on the basis of the distance image and the reference distance information.

According to the present disclosure, it is possible to perform determination related to an attachable and detachable member attached to a radiography apparatus with a simple configuration.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the invention will be described in detail with reference to the drawings. Each of the embodiments does not limit the invention.

Figure 1:
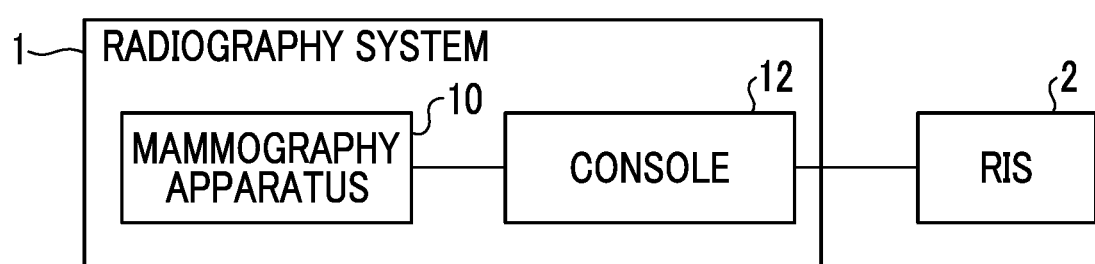
FIG. 1 is a schematic diagram illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of an information processing apparatus according to the present disclosure.

Figure 2:
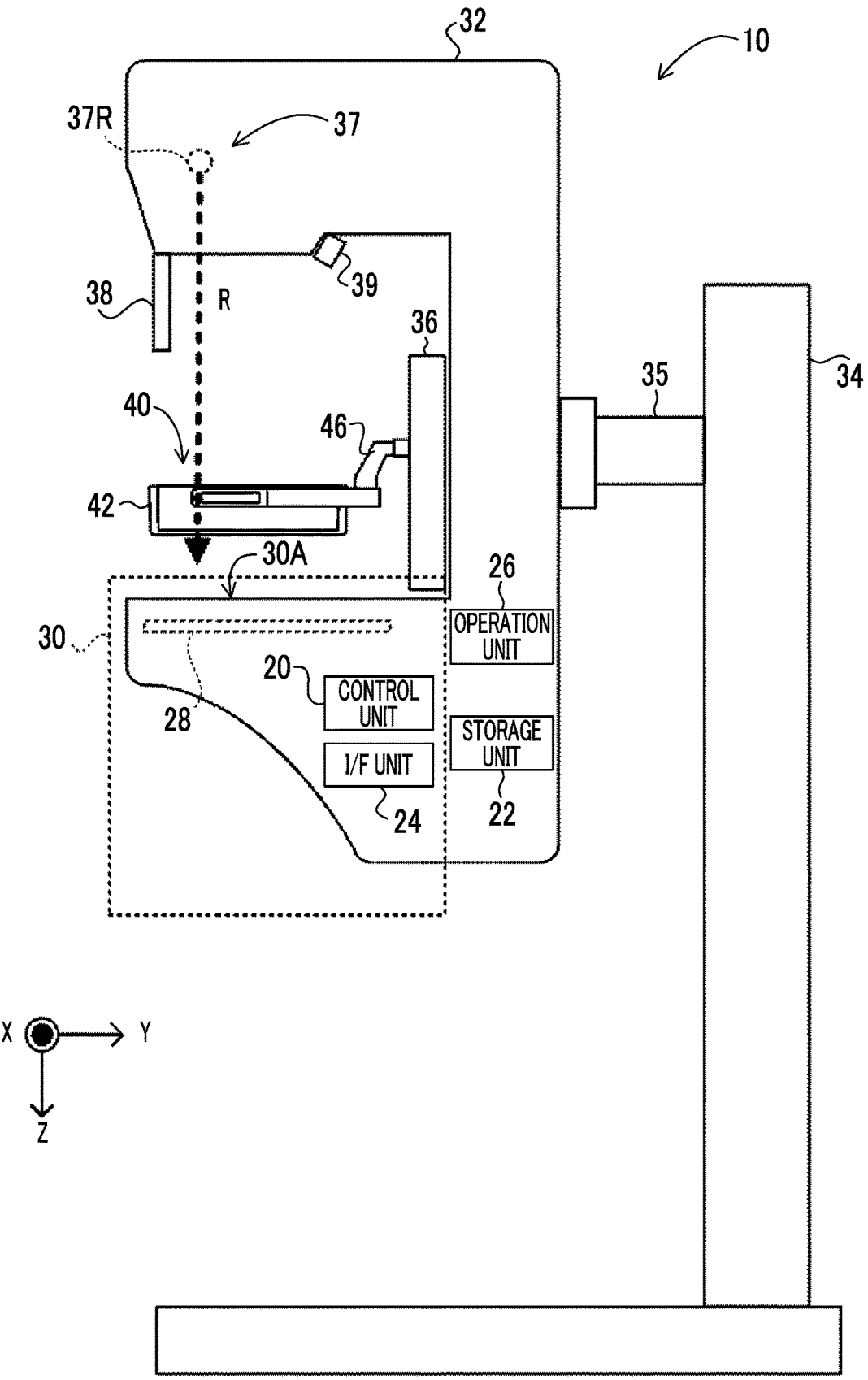
FIG. 2 is a side view illustrating an example of the outward appearance of a mammography apparatus according to the embodiment.

First, the mammography apparatus 10 according to this embodiment will be described. FIG. 2 is a side view illustrating an example of the outward appearance of the mammography apparatus 10 according to this embodiment. In addition, FIG. 2 illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

As illustrated in FIG. 2, the mammography apparatus 10 according to this embodiment comprises a control unit 20, a storage unit 22, and an interface (I/F) unit 24 which are provided in an imaging table 30. The control unit 20 controls the overall operation of the mammography apparatus 10 under the control of the console 12. The control unit 20 comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data.

For example, image data of the radiographic image captured by a radiation detector 28 and various other kinds of information are stored in the storage unit 22. Examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, an operation unit 26 is provided as a plurality of switches in, for example, the imaging table 30 of the mammography apparatus 10. Further, the operation unit 26 may be provided as a touch panel switch or may be provided as a foot switch that is operated by the user's feet.

The radiation detector 28 detects the radiation R transmitted through the breast which is the object. As illustrated in FIG. 2, the radiation detector 28 is disposed in the imaging table 30. In the mammography apparatus 10 according to this embodiment, in a case in which imaging is performed, the breast of the subject is positioned on an imaging surface 30A of the imaging table 30 by a user such as a doctor or a radiology technician.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2, the radiation emitting unit 37 is provided in an arm portion 32 together with the imaging table 30 and a compression unit 36. As illustrated in FIG. 2, a face guard 38 is attachable to and detachable from a position of the arm portion 32 which is close to the subject below the radiation emitting unit 37. The face guard 38 is a protective member for protecting the subject from the radiation R emitted from the radiation source 37R.

Further, a time-of-flight (TOF) camera 39 that captures a distance image indicating the distance to an imaging target is provided at a position of the arm portion 32 which is away from the subject below the radiation emitting unit 37. The TOF camera 39 is a camera that captures a distance image using a TOF method and is an example of an imaging device according to the present disclosure. Specifically, the TOF camera 39 emits light, such as infrared rays, to the imaging target and measures the distance between the TOF camera 39 and the imaging target on the basis of the time until reflected light is received or a phase change between the emitted light and the received light. In the distance image captured by the TOF camera 39, each pixel has distance information indicating the distance between the TOF camera 39 and the imaging target. In addition, the distance image means an image from which the distance to the imaging target can be derived.

In addition, as illustrated in FIG. 2, the mammography apparatus 10 according to this embodiment comprises the arm portion 32, a base 34, and a shaft portion 35. The arm portion 32 is held by the base 34 so as to be movable in the up-down direction (Z-axis direction). The shaft portion 35 connects the arm portion 32 to the base 34. In addition, the arm portion 32 can be relatively rotated with respect to the base 34, using the shaft portion 35 as a rotation axis.

Each of the arm portion 32, the imaging table 30, and the compression unit 36 can be relatively rotated with respect to the base 34, using the shaft portion 35 as a rotation axis. In this embodiment, engagement portions (not illustrated) are provided in each of the base 34, the arm portion 32, the imaging table 30, and the compression unit 36. The state of the engagement portions is switched to connect each of the arm portion 32, the imaging table 30, and the compression unit 36 to the base 34. The arm portion 32, the imaging table 30, and the compression unit 36 connected to the shaft portion 35 are integrally rotated on the shaft portion 35.

The compression unit 36 is provided with a compression plate driving unit (not illustrated) that moves a compression plate 40 in the up-down direction (Z-axis direction). The compression plate 40 according to this embodiment has a function of compressing the breast of the subject. A support portion 46 of the compression plate 40 is detachably attached to the compression plate driving unit and is moved in the up-down direction (Z-axis direction) by the compression plate driving unit to compress the breast of the subject between the compression plate 40 and the imaging table 30. The compression plate 40 according to this embodiment is an example of an attachable and detachable member according to the present disclosure and is also an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for magnification imaging.

As a specific example, three types of compression plates $40_1$ to $40_3$ that can be attached to the mammography apparatus 10 according to this embodiment will be described with reference to FIGS. 3A to 3C, respectively. In addition, for the compression plate 40 according to this embodiment, in a case in which the compression plates $40_1$ to $40_3$ are generically referred to regardless of the type, for example, reference numerals 1 to 3 indicating the types in the compression plates $40_1$ to $40_3$ are omitted, and the compression plates $40_1$ to $40_3$ are simply referred to as "compression plates 40".

Figure 3A:
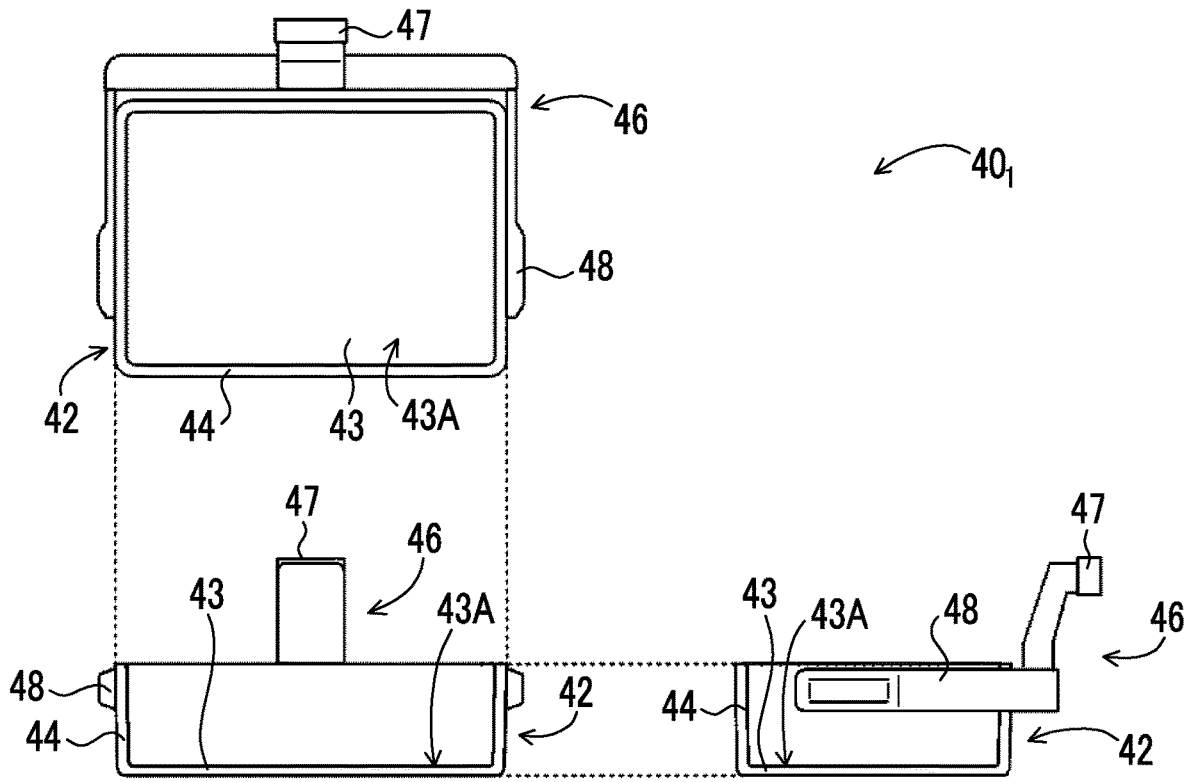
FIG. 3A is a three-view diagram illustrating an example of a compression plate according to the embodiment.

FIG. 3A is a three-view diagram illustrating an example of the compression plate $40_1$ according to this embodiment. The three-view diagram illustrated in FIG. 3A includes a plan view (top view) of the compression plate $40_1$ viewed from the upper side (from the radiation emitting unit 37), a side view of the compression plate $40_1$ viewed from the subject, and a side view of the compression plate $40_1$ viewed from the right side of the subject. As illustrated in FIG. 3A, the compression plate $40_1$ according to this embodiment includes a compression portion 42 and a support portion 46.

The compression portion 42 is formed in a concave shape in a cross-sectional view in which a bottom portion 43 is surrounded by a wall portion 44. In the bottom portion 43, the thickness of a plate having a surface that comes into contact with the breast of the subject is substantially constant, and an upper surface 43A that faces the radiation source 37R is flat and has a substantially uniform height. Further, the wall portion 44 is relatively high and has a substantially uniform height. It is preferable that the compression portion 42 is optically transparent in order to check positioning or a compressed state in the compression of the breast. In addition, the compression portion 42 is made of a material having high transmittance for the radiation R. Specific examples of the material include polycarbonate (PC) and polyethylene terephthalate (PRT), acrylic, and polypropylene (PP). However, the material is not particularly limited.

On the other hand, the support portion 46 includes an attachment portion 47 and an arm 48. The attachment portion 47 has a function of attaching the compression plate 40 to the mammography apparatus 10, specifically, the compression plate driving unit in the compression plate 40. The arm 48 has a function of supporting the compression portion 42.

Figure 3B:
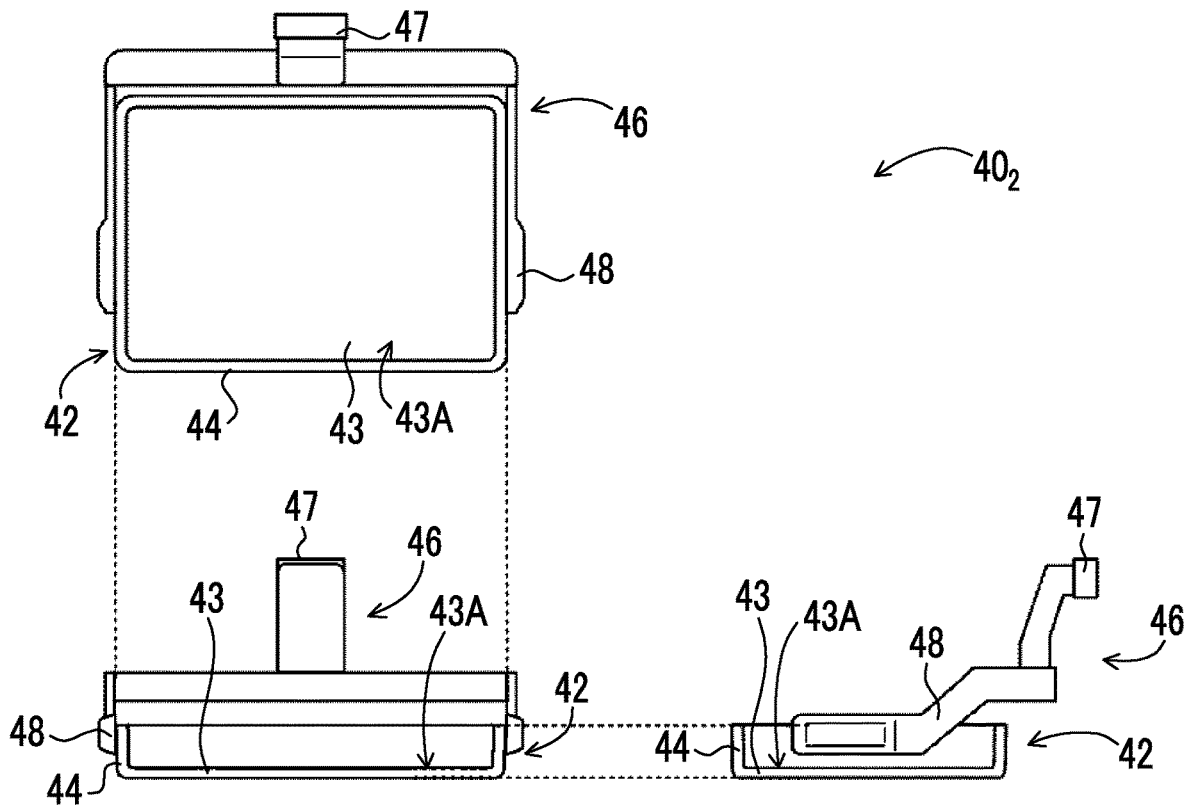
FIG. 3B is a three-view diagram illustrating another example of the compression plate according to the embodiment.

FIG. 3B is a three-view diagram illustrating an example of the compression plate $40_2$ according to this embodiment. The three-view diagram illustrated in FIG. 3B includes a plan view (top view) of the compression plate $40_2$ viewed from the upper side (from the radiation emitting unit 37), a side view of the compression plate $40_2$ viewed from the subject, and a side view of the compression plate $40_2$ viewed from the right side of the subject. As illustrated in FIG. 3B, the compression plate $40_2$ according to this embodiment includes a compression portion 42 and a support portion 46, similarly to the compression plate $40_k$. As illustrated in FIG. 3B, the compression plate $40_2$ according to this embodiment has the same configuration as the compression plate $40_1$ except that the height of a wall portion 44 is lower than the height of the wall portion 44 of the compression plate $40_1$ illustrated in FIG. 3A and the shape of an arm 48 of the support portion 46 is different.

Figure 3C:
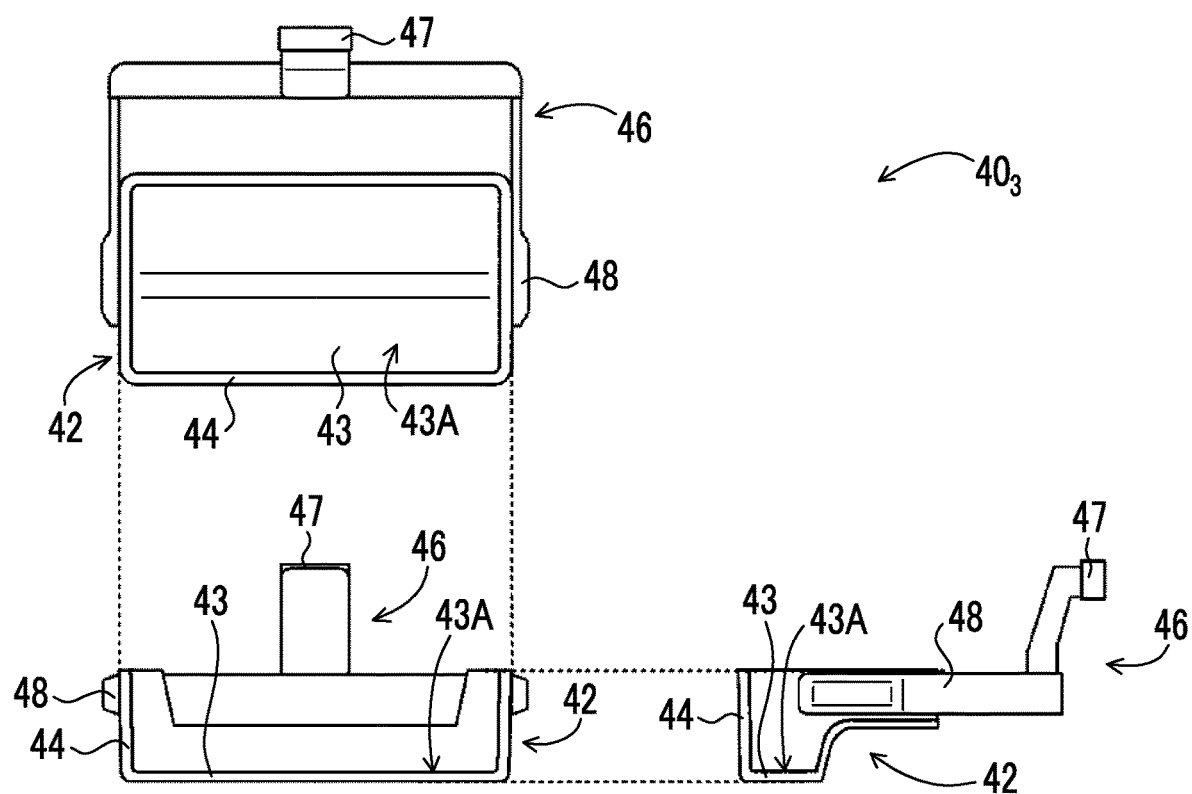
FIG. 3C is a three-view diagram illustrating still another example of the compression plate according to the embodiment.

FIG. 3C is a three-view diagram illustrating an example of the compression plate $40_3$ according to this embodiment. The three-view diagram illustrated in FIG. 3C includes a plan view (top view) of the compression plate $40_3$ viewed from the upper side (from the radiation emitting unit 37), a side view of the compression plate $40_3$ viewed from the subject, and a side view of the compression plate $40_3$ viewed from the right side of the subject. As illustrated in FIG. 3C, the compression plate $40_3$ according to this embodiment includes a compression portion 42 and a support portion 46, similarly to the compression plates $40_1$ and $40_2$. As illustrated in FIG. 3C, an upper surface 43A of a bottom portion 43 of the compression plate $40_3$ according to this embodiment is not flat. In the upper surface 43A, a portion close to the attachment portion 47 is higher than a portion (a portion away from the attachment portion 47) close to the chest wall. Further, the height of the wall portion 44 is not uniform. In the wall portion 44, the height of a portion close to the chest wall is lower than the height of the other portions.

As such, in the compression plate $40_1$, the upper surface 43A of the bottom portion 43 is flat, and the height of the wall portion 44 is uniform and is relatively large. Therefore, in a case in which the image of the compression plate $40_1$ is captured from directly above by the TOF camera 39, the distance between the TOF camera 39 and the upper surface 43A is substantially constant regardless of place. In addition, the distance between the TOF camera 39 and the wall portion 44 is substantially constant regardless of place and is shorter than the distance between the TOF camera 39 and the wall 44 in the compression plate $40_2$. On the other hand, in the compression plate $40_2$, the upper surface 43A of the bottom portion 43 is flat, and the height of the wall portion 44 is uniform and is relatively small. Therefore, in a case in which the image of the compression plate $40_2$ is captured from directly above by the TOF camera 39, the distance between the TOF camera 39 and the upper surface 43A is substantially constant regardless of place. In addition, the distance between the TOF camera 39 and the wall portion 44 is substantially constant regardless of place and is longer than the distance between the TOF camera 39 and the wall 44 in the compression plate $40_k$. On the other hand, in the compression plate $40_3$, the upper surface 43A of the bottom portion 43 is not flat, and the height of the wall portion 44 is not uniform. Therefore, in a case in which the image of the compression plate $40_3$ is captured from directly above by the TOF camera 39, the distance between the TOF camera 39 and the upper surface 43A in the portion close to the attachment portion 47 is shorter than that in the portion close to the chest wall. Further, the distance between the TOF camera 39 and the wall portion 44 in a central portion close to the chest wall is longer than that in the other portions.

Therefore, the distance between the compression plate 40 and the TOF camera 39 can be measured by the TOF camera 39 to distinguish the compression plates $40_1$ to $40_3$.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

Figure 4:
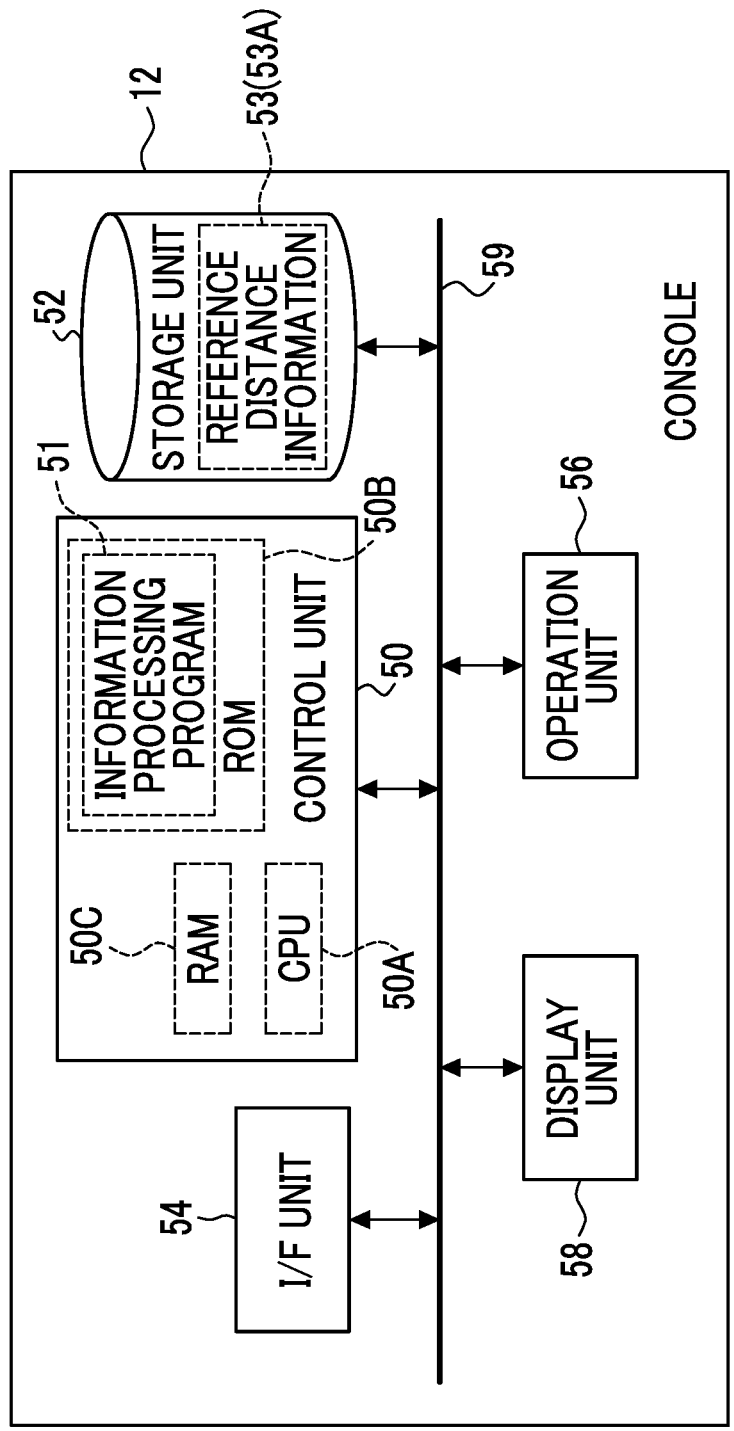
FIG. 4 is a block diagram illustrating an example of the configuration of a console according to the embodiment.

For example, the console 12 according to this embodiment is a server computer. As illustrated in FIG. 4, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including an information processing program 51 (which will be described below) executed by the CPU 50A are stored in the ROM 50B in advance. The RAM 50C temporarily stores various kinds of data. The CPU 50A according to this embodiment is an example of a processor according to the present disclosure, and the ROM 50B according to this embodiment is an example of a memory according to the present disclosure.

For example, the image data of the radiographic image captured by the mammography apparatus 10 and various other kinds of information are stored in the storage unit 52. An HDD or an SSD is given as a specific example of the storage unit 52. Further, the storage unit 52 according to this embodiment stores reference distance information 53 which will be described in detail below.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 5:
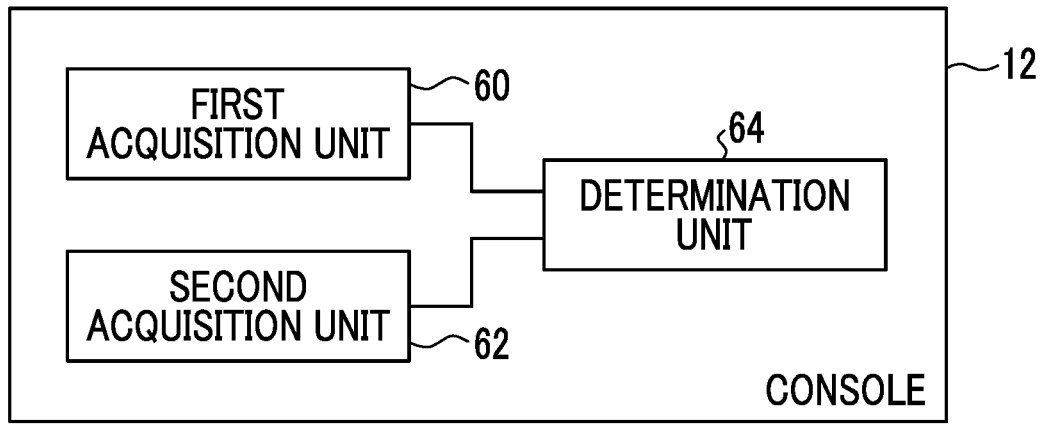
FIG. 5 is a functional block diagram illustrating an example of the function of the console according to the embodiment.

FIG. 5 is a functional block diagram illustrating an example of the configuration of the console 12 according to this embodiment. As illustrated in FIG. 5, the console 12 comprises a first acquisition unit 60, a second acquisition unit 62, and a determination unit 64. For example, in the console 12 according to this embodiment, the CPU 50A of the control unit 50 executes the information processing program 51 stored in the ROM 50B to function as the first acquisition unit 60, the second acquisition unit 62, and the determination unit 64.

The first acquisition unit 60 has a function of acquiring the distance image captured by the TOF camera 39. For example, the first acquisition unit 60 according to this embodiment acquires image data indicating the distance image captured by the TOF camera 39 from the TOF camera 39 through the I/F unit 24 and the I/F unit 54.

The second acquisition unit 62 has a function of acquiring the reference distance information 53. For example, the second acquisition unit 62 according to this embodiment acquires the reference distance information 53 from the storage unit 52. The reference distance information 53 is information related to the reference value of the distance between the compression plate 40 and the TOF camera 39 in a state in which the compression plate 40 is attached to the mammography apparatus 10. The reference distance information 53 according to this embodiment is an example of reference distance information related to a reference value according to the present disclosure. In this embodiment, the distance between the compression plate 40 and the TOF camera 39 in a case in which the position where the compression plate 40 is attached to the mammography apparatus 10 is an initial position is applied as the reference value of the distance between the compression plate 40 and the TOF camera 39. In addition, an example of the initial position of the compression plate 40 is a position closest to the imaging table 30. Further, a reference distance map 53A (see also FIG. 11) showing the reference value of the distance between the compression plate 40 and the TOF camera 39 is applied as the reference distance information 53. The reference distance map 53A exists for each type of the compression plate 40. In this embodiment, since there are a plurality of types of compression plates 40 as described above, a plurality of reference distance maps 53A are stored as the reference distance information 53 in the storage unit 52. Further, in this embodiment, a reference distance map 53A corresponding to a state in which the compression plate 40 is not attached to the mammography apparatus 10 is also stored as the reference distance information 53 in the storage unit 52.

In this embodiment, a "map", such as the reference distance map 53A or a distance map 72 (see FIG. 10) for the distance image, is information in which the distance information indicated by each pixel of the distance image or a divided grid (see FIG. 9 and the like) is associated with the position of the pixel, the grid, or the like. The reference distance map 53A may not be the image and may be, for example, a table indicating the correlation between the position of the pixel, the grid, or the like and the distance information as long as it is the information in which the position of the pixel, the grid, or the like is associated with the distance information.

Further, the reference distance map 53A may be any information indicating the reference value of the distance between the compression plate 40 and the TOF camera 39 in the distance image. For example, the reference distance map 53A may be the distance image or an image obtained by processing the distance image. For example, in this embodiment, the image obtained by processing the distance image is used. In this embodiment, a distance image 70 (see FIG. 9) is divided in a grid pattern, and the distance map 72 (see FIG. 10) in which distance information is digitized for each grid is used for an attachable and detachable member determination process (see FIG. 7), which will be described in detail below. Therefore, similarly to the distance map 72, the distance image is divided in a grid pattern, and an image in which distance information for each grid is digitized is used as the reference distance map 53A.

The reference distance information 53 can be obtained on the basis of the distance image or the like captured by the TOF camera 39 or the like in advance in a state in which the compression plate 40 attached to the mammography apparatus 10 is at the initial position. In addition, in this embodiment, the aspect in which the reference distance information 53 is stored in the storage unit 52 of the console 12 has been described. However, the place in which the reference distance information 53 is stored is not limited to the storage unit 52. For example, the reference distance information 53 may be stored in the storage unit 22 of the mammography apparatus 10 or may be stored in a device outside the radiography system 1.

The determination unit 64 has a function of determining whether or not the compression plate 40 is attached to the mammography apparatus 10 on the basis of the distance image and the reference distance information 53. Further, the determination unit 64 according to this embodiment has a function of determining the type of the compression plate 40 in a case in which the compression plate 40 is attached to the mammography apparatus 10.

Next, the operation of the console 12 according to this embodiment will be described with reference to the drawings.

Figure 6:
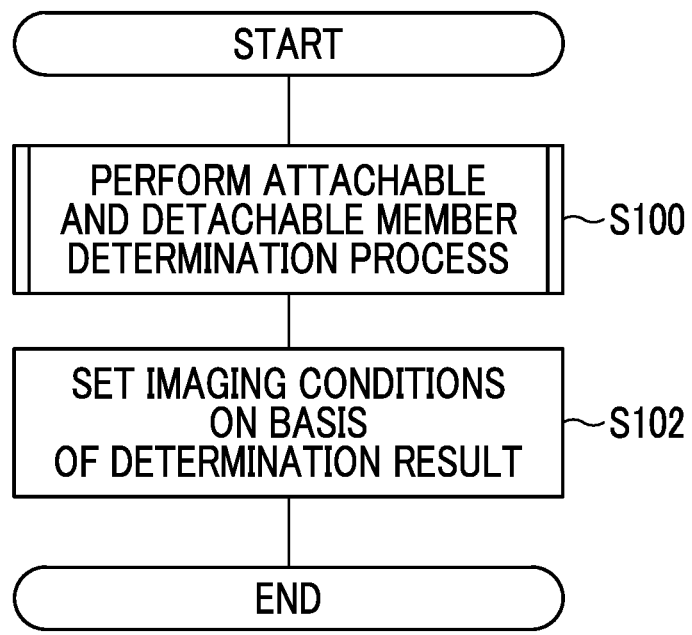
FIG. 6 is a flowchart illustrating an example of the flow of information processing in the console according to the embodiment.

For example, in a case in which the console 12 according to this embodiment receives an imaging order from the RIS 2 or the like, the CPU 50A of the control unit 50 executes the information processing program 51 stored in the ROM 50B to perform the information processing whose example is illustrated in FIG. 6. FIG. 6 is a flowchart illustrating an example of the flow of the image processing performed in the console 12 according to this embodiment.

Figure 7:
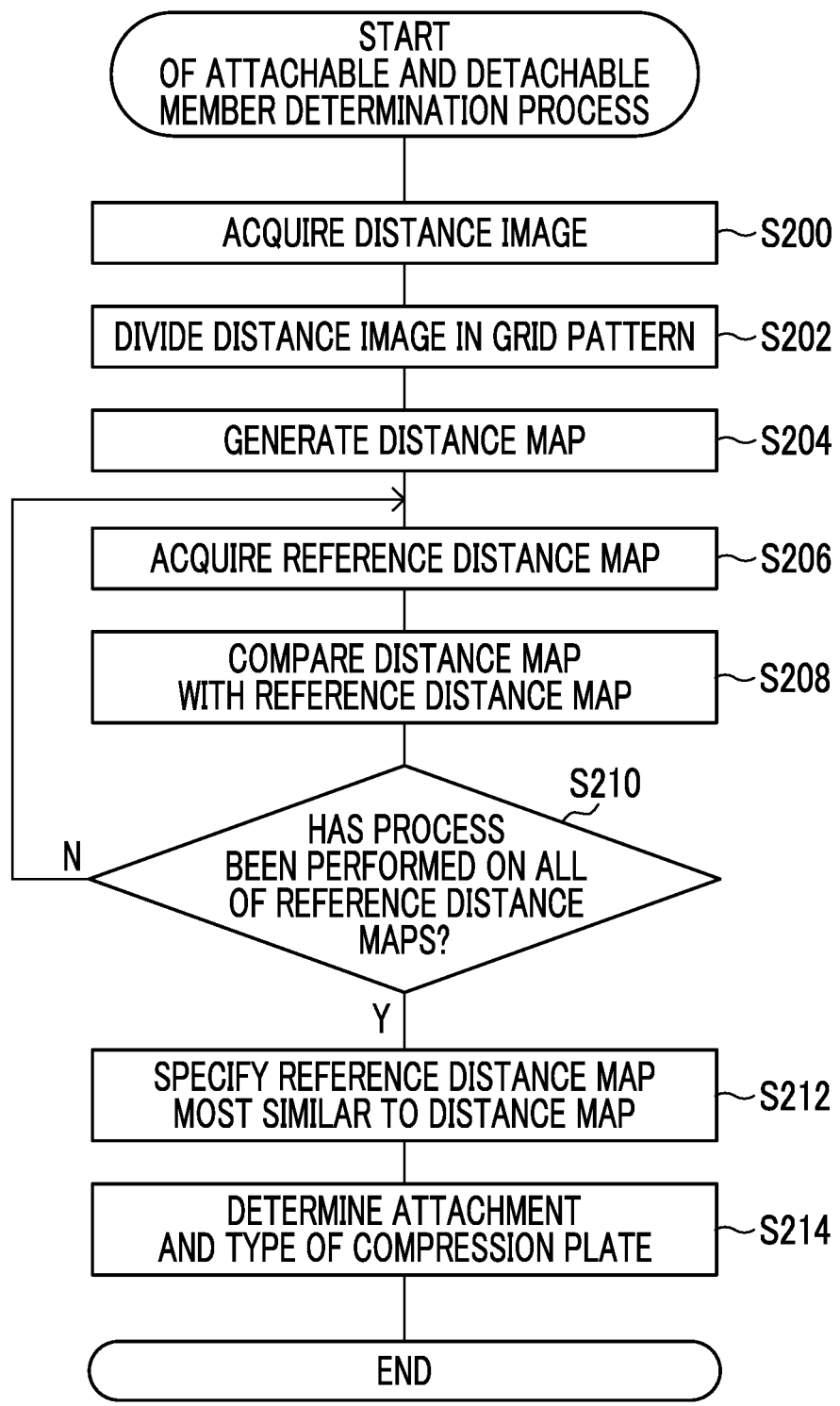
FIG. 7 is a flowchart illustrating an example of the flow of an attachable and detachable member determination process performed in the information processing.

In Step S100 of FIG. 6, the attachable and detachable member determination process illustrated in FIG. 7 is performed to determine whether or not the compression plate 40 is attached to the mammography apparatus 10. FIG. 7 is a flowchart illustrating an example of the flow of the attachable and detachable member determination process.

In Step S200 of FIG. 7, the first acquisition unit 60 acquires the distance image from the TOF camera 39 of the mammography apparatus 10. Specifically, the first acquisition unit 60 instructs the TOF camera 39 to capture a distance image and acquires the distance image captured by the TOF camera 39 on the basis of the instruction through the I/F unit 24. The distance image acquired by the first acquisition unit 60 is output to the determination unit 64.

Figure 8A:
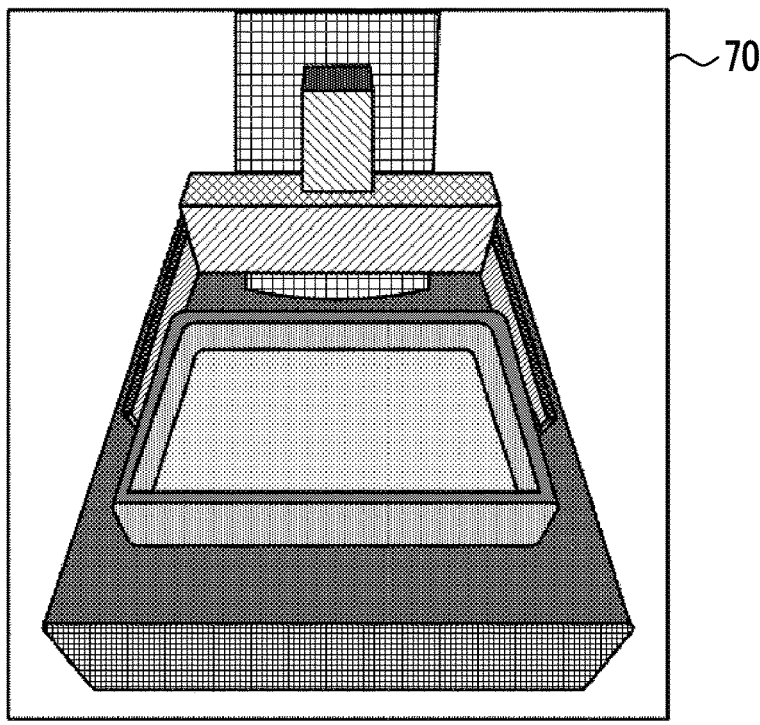
FIG. 8A is a schematic diagram illustrating an example of a distance image acquired by a first acquisition unit.
Figure 8B:
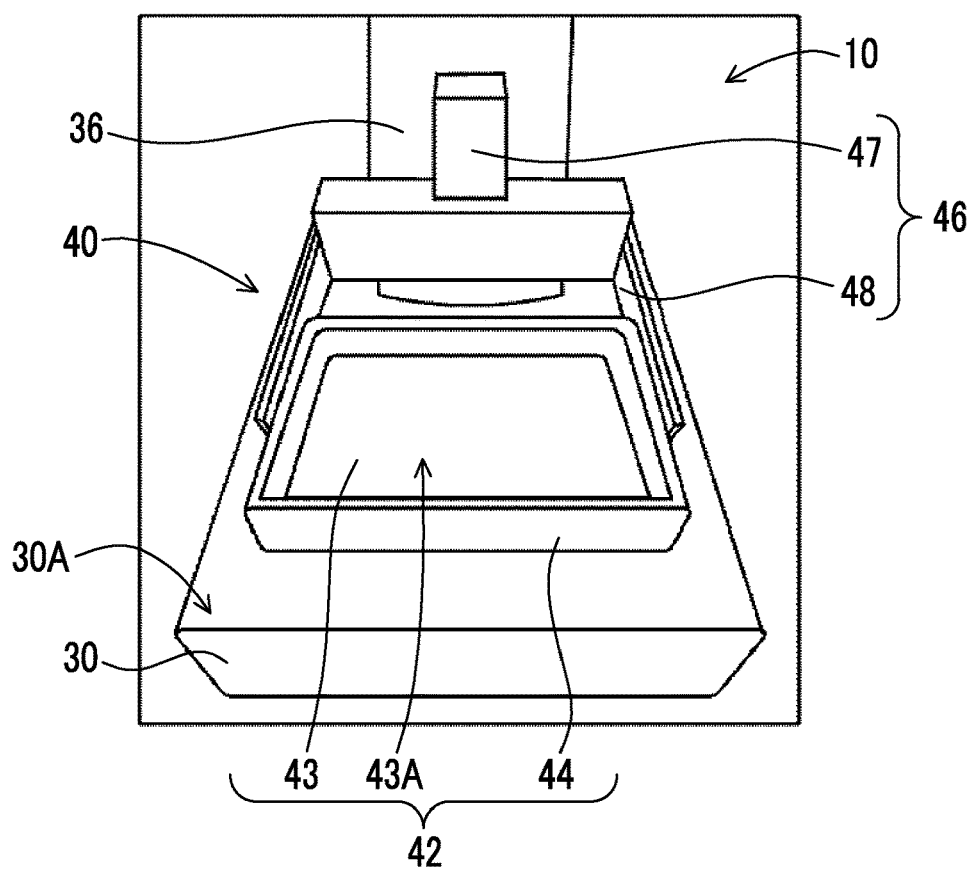
FIG. 8B is a schematic diagram illustrating an example of a visible light image captured by a visible light camera from the same position as a TOF camera.

FIG. 8A is a schematic diagram illustrating an example of the distance image 70 acquired by the first acquisition unit 60. Further, FIG. 8B is a schematic diagram illustrating an example of a visible light image captured by a visible light camera, that is, a so-called general camera from the same position as the TOF camera 39. In addition, for convenience of explanation, FIG. 8A is a schematic diagram illustrating an example of the distance image 70 captured by a TOF camera 39, which is different from the TOF camera 39 illustrated in FIG. 2 and is disposed close to the face guard 38 of the radiation emitting unit 37, in a direction toward the compression unit 36. Even in this case, the same process is performed regardless of the disposition of the TOF camera 39. Therefore, hereinafter, the description will be made using the distance image 70 illustrated in FIG. 8A.

Further, in this embodiment, the distance image is captured by the TOF camera 39 before the subject is positioned. In a state in which the subject is positioned and the breast of the subject is compressed by the compression plate 40, the distance between the TOF camera 39 and the compression plate 40 changes depending on the thickness of the breast. Therefore, in a case in which it is determined whether or not the compression plate 40 is attached, it is preferable that the distance image is captured by the TOF camera 39 before the subject is positioned.

Figure 9:
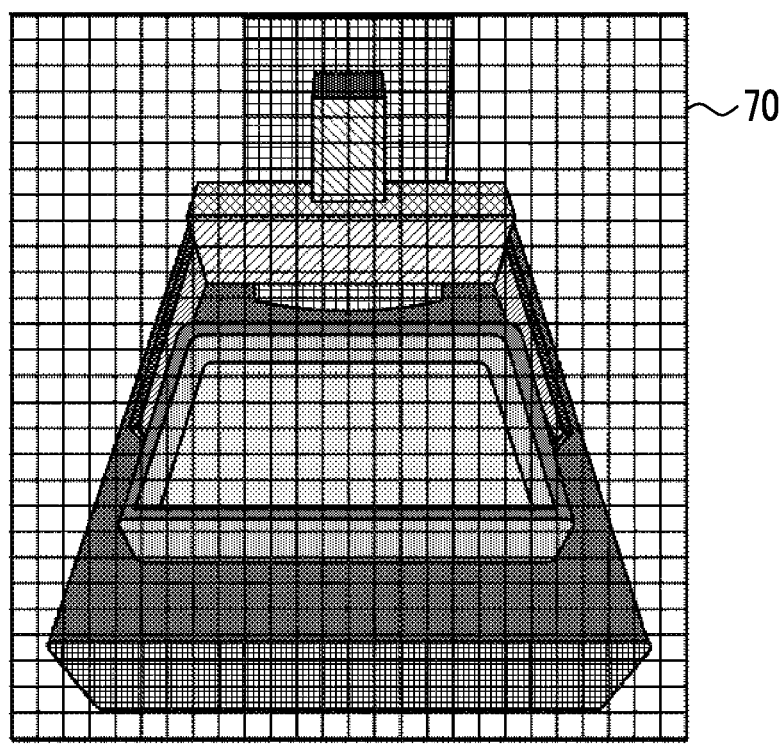
FIG. 9 is a schematic diagram illustrating an example in which a distance image is divided in a grid pattern.

Then, in Step S202, the determination unit 64 divides the distance image 70 in a grid pattern. FIG. 9 is a schematic diagram illustrating an example in which the distance image 70 is divided in a grid pattern. The size of the grid is not limited, and the grid may have any size. In addition, as the size of the grid becomes smaller, accuracy becomes higher, but a processing speed becomes lower.

Figure 10:
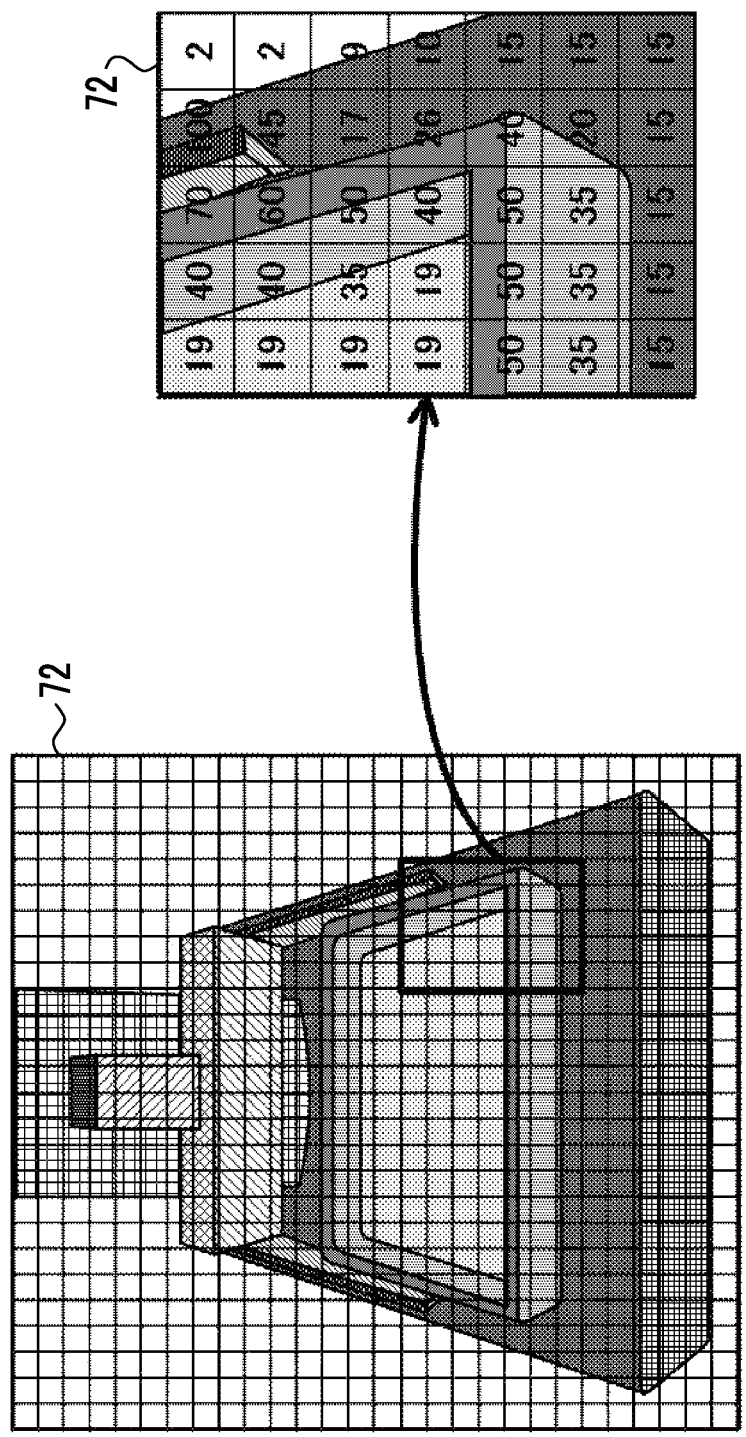
FIG. 10 is a schematic diagram illustrating an example of a distance map generated by a determination unit.

Then, in Step S204, the determination unit 64 digitizes and maps the distance information for each divided grid in the distance image 70 to generate a distance map. FIG. 10 illustrates an example of the distance map 72 generated by the determination unit 64. In addition, in FIG. 10, the digitized distance information is clearly illustrated in a partially enlarged view of the distance map 72.

Further, FIG. 10 illustrates an example in a case in which, in the distance image 70, the distance information of an imaging target that is closest to the TOF camera 39 is set to "0", the distance information of an imaging target that is farthest from the TOF camera 39 is set to "255", and the value becomes larger as the distance to the TOF camera 39 becomes longer.

Furthermore, a method for digitizing the distance information for each grid of the distance image 70 in the determination unit 64 is not limited. For example, for each grid, the average value of the distance information of a plurality of pixels included in the grid may be used as the distance information of the grid.

Then, in Step S206, the second acquisition unit 62 acquires the reference distance map 53A. Specifically, the second acquisition unit 62 acquires one of the plurality of reference distance maps 53A stored in the storage unit 52. The acquired reference distance map 53A is output to the determination unit 64.

Figure 11:
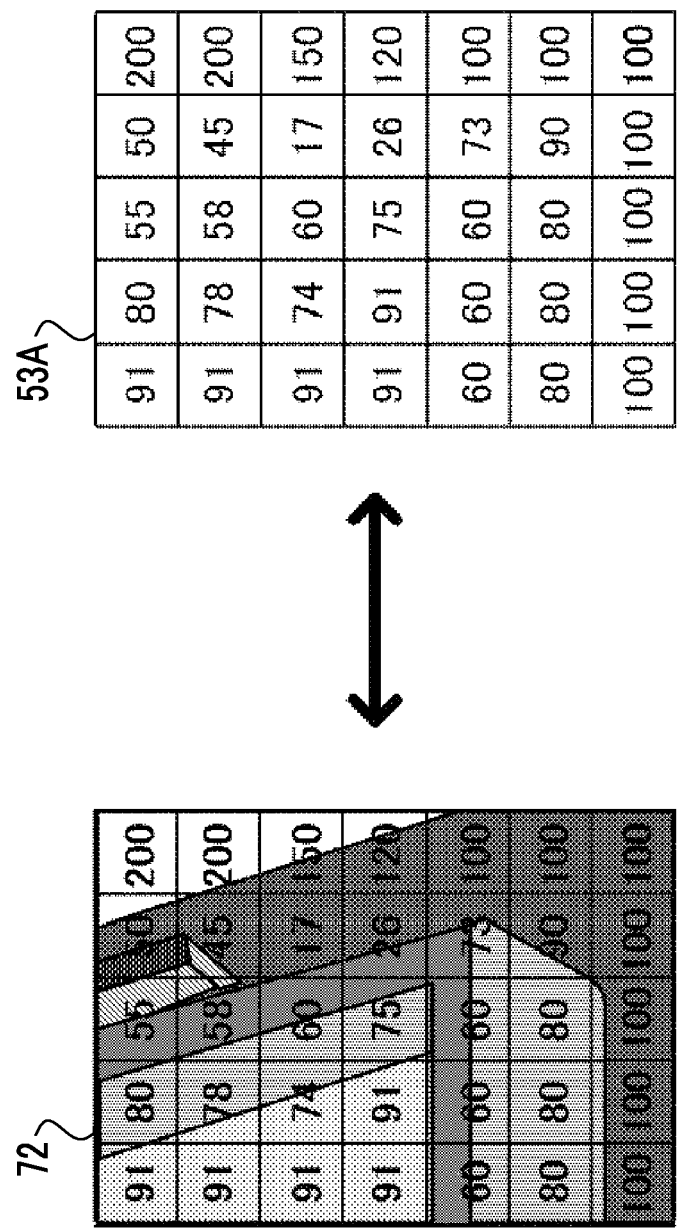
FIG. 11 is a diagram illustrating a comparison between a reference distance map and a distance map by the determination unit.

Then, in Step S208, the determination unit 64 compares the acquired reference distance map 53A with the distance map 72 generated in Step S204 as illustrated in FIG. 11. The determination unit 64 derives the similarity between the reference distance map 53A and the distance map 72 as an example of the comparison result. In addition, the entire distance map 72 and the entire reference distance map 53A may be set as the comparison target. However, instead of comparing the entire maps, partial regions including the image of the attachable and detachable member may be set as the comparison target. In this embodiment, as described above, the position of the compression plate 40 in a case in which the distance image 70 is captured is defined as the initial position. Therefore, it is possible to specify the region of the image indicating the compression plate 40 included in the distance image 70 in advance. In this case, the region of the image indicating the compression plate 40 included in the distance image 70 can be set as the comparison target to increase the accuracy of comparison and to reduce the processing time for comparison.

Then, in Step S210, the determination unit 64 determines whether or not the process in Steps S206 and S208 has been performed on all of the reference distance maps 53A stored in the storage unit 52. In a case in which there is a reference distance map 53A that has not been subjected to the process in Steps S206 and S208, the determination result in Step S210 is "No", and the process returns to Step S206. Then, the process in Steps S206 and S208 is repeated. On the other hand, in a case in which the process in Steps S206 and S208 has been performed on all of the reference distance maps 53A, the determination result in Step S210 is "Yes", and the process proceeds to Step S212.

In Step S212, the determination unit 64 specifies the reference distance map 53A that is most similar to the distance map 72 on the basis of the comparison result in Step S208.

Then, in Step S214, the determination unit 64 determines whether or not the compression plate 40 is attached to the mammography apparatus 10 on the basis of the reference distance map 53A specified in Step S212 and determines the type of the attached compression plate 40 in a case in which the compression plate 40 is attached.

Specifically, in a case in which the most similar reference distance map 53A is the reference distance map 53A corresponding to a state in which the compression plate 40 is not attached to the mammography apparatus 10, the determination unit 64 determines that the compression plate 40 is not attached to the mammography apparatus 10. In the other cases, the determination unit 64 determines that the compression plate 40 is attached to the mammography apparatus 10 and specifies the type of the compression plate 40 corresponding to the most similar reference distance map 53A as the type of the compression plate 40 attached to the mammography apparatus 10. In a case in which the process in Step S214 ends, the attachable and detachable member determination process illustrated in FIG. 7 ends, and Step S100 of the information processing illustrated in FIG. 6 ends. Then, the process proceeds to Step S102.

In addition, a method for determining the type of the attachable and detachable member attached to the mammography apparatus 10, specifically, the attachable and detachable member determination process is not limited to the aspect described above with reference to FIG. 7. For example, the following method may be used. The determination unit 64 derives a difference in distance indicated by the distance information for each grid corresponding to the same position in the reference distance map 53A and the distance map 72, and derives the sum of the absolute values of the differences derived for all of the grids. In a case in which the derived sum is equal to or less than a predetermined threshold value, the determination unit 64 determines that the compression plate 40 corresponding to the reference distance map 53A used for the derivation is attached to the mammography apparatus 10. In contrast, in a case in which the derived sum is equal to or less than the predetermined threshold value, the determination unit 64 may determine that the compression plate 40 corresponding to the reference distance map 53A used for the derivation is not attached to the mammography apparatus 10. Further, in the case of this aspect, for example, in a case in which a new type of compression plate 40 is attached to the mammography apparatus 10, the derived sum is equal to or less than the predetermined threshold value for all of the reference distance maps 53A stored in the storage unit 52. As such, in a case in which the derived sum is equal to or less than the predetermined threshold value for all of the reference distance maps 53A stored in the storage unit 52, the determination unit 64 is not capable of determining the type of the compression plate 40 attached to the mammography apparatus 10. Therefore, for example, the determination unit 64 may output information indicating a warning.

Further, in the above-described aspect, the distance image 70 is divided in a grid pattern to generate the distance map 72, and the distance map 72 is used for the determination. However, the distance image 70 may be used for the determination. In this case, instead of the grids, the distance information indicated by each pixel, such as the pixel value of each pixel of the distance image 70, may be used for the determination.

In Step S102, the determination unit 64 sets imaging conditions for the radiographic image on the basis of the result of the attachable and detachable member determination process in Step S100. In some cases, the imaging conditions are determined according to the member attached to the mammography apparatus 10. For example, in some cases, the size of an irradiation field which is an example of the imaging conditions is determined according to the type of the compression plate 40. In this case, the determination unit 64 acquires the size of the irradiation field determined according to the type of the compression plate 40 obtained as the determination result, and controls a collimator (not illustrated) of the radiation emitting unit 37 or the like in order to obtain the acquired size of the irradiation field. In a case in which the process in Step S102 ends, the information processing illustrated in FIG. 6 ends.

As such, in this embodiment, the console 12 acquires the distance image 70 captured by the TOF camera 39, determines whether or not the compression plate 40 is attached to the mammography apparatus 10 on the basis of the result of the comparison between the distance map 72 generated from the distance image and the reference distance map 53A which is the reference distance information 53, and determines the type of the compression plate 40 in a case in which the compression plate 40 is attached.

In addition, the present disclosure is not limited to the above-described aspect. For example, the following Modification Examples 1 and 2 may be applied.

Modification Example 1

In this modification example, a modification example of the reference distance information 53 will be described. As described above, the compression plates $40_1$ to $40_3$ can be identified by the wall portion 44 and the upper surface 43A of the bottom portion 43. Therefore, a region including the wall portion 44 and the upper surface 43A of the bottom portion 43 of the compression plate 40 required for identification in the distance image 70 is compared with the reference distance information 53 to determine whether or not the compression plate 40 is attached and to determine the type of the compression plate 40 in a case in which the compression plate 40 is attached. In this modification example, this aspect will be described.

Figure 12A:
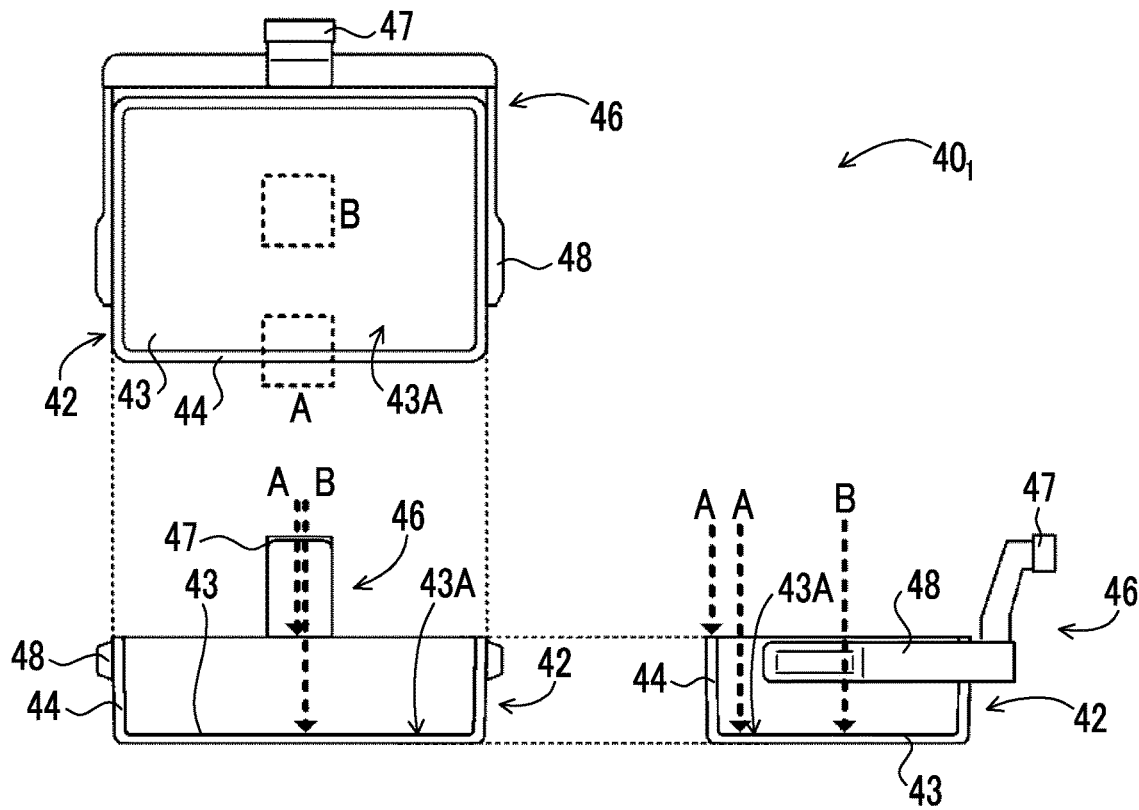
FIG. 12A is a three-view diagram illustrating an example of a compression plate for explaining Modification Example 1.
Figure 12B:
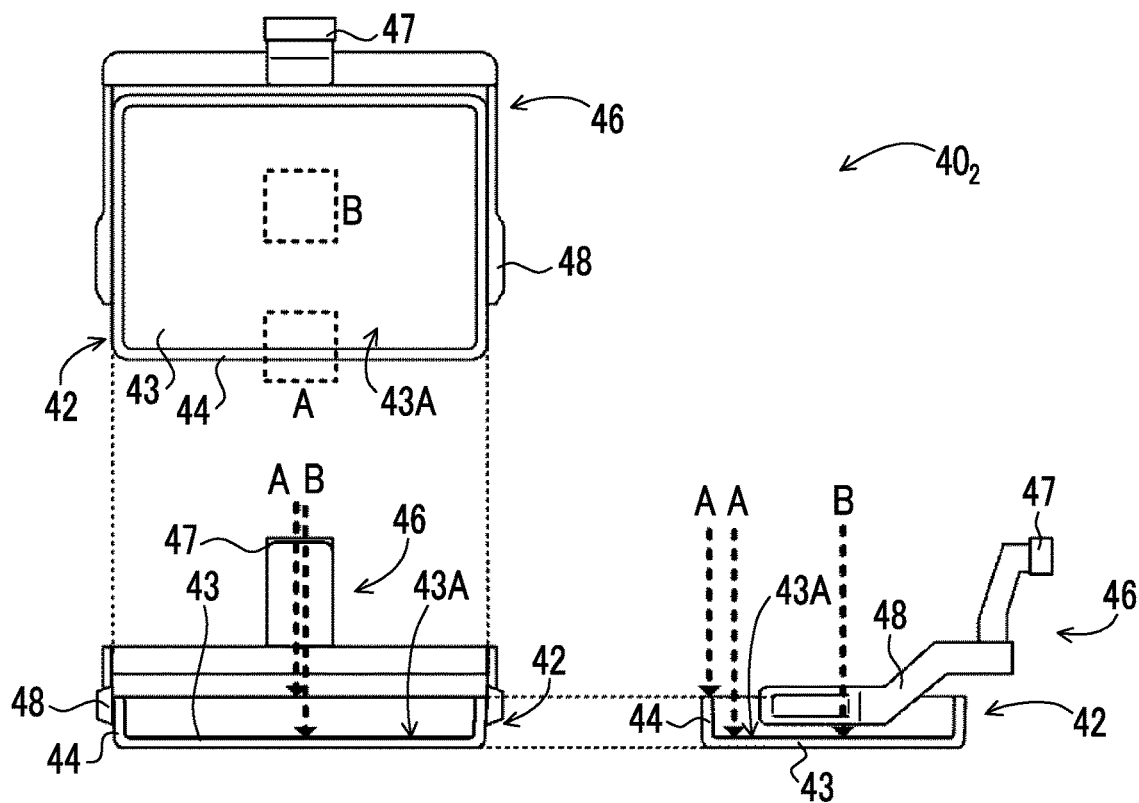
FIG. 12B is a three-view diagram illustrating another example of the compression plate for explaining Modification Example 1.
Figure 12C:
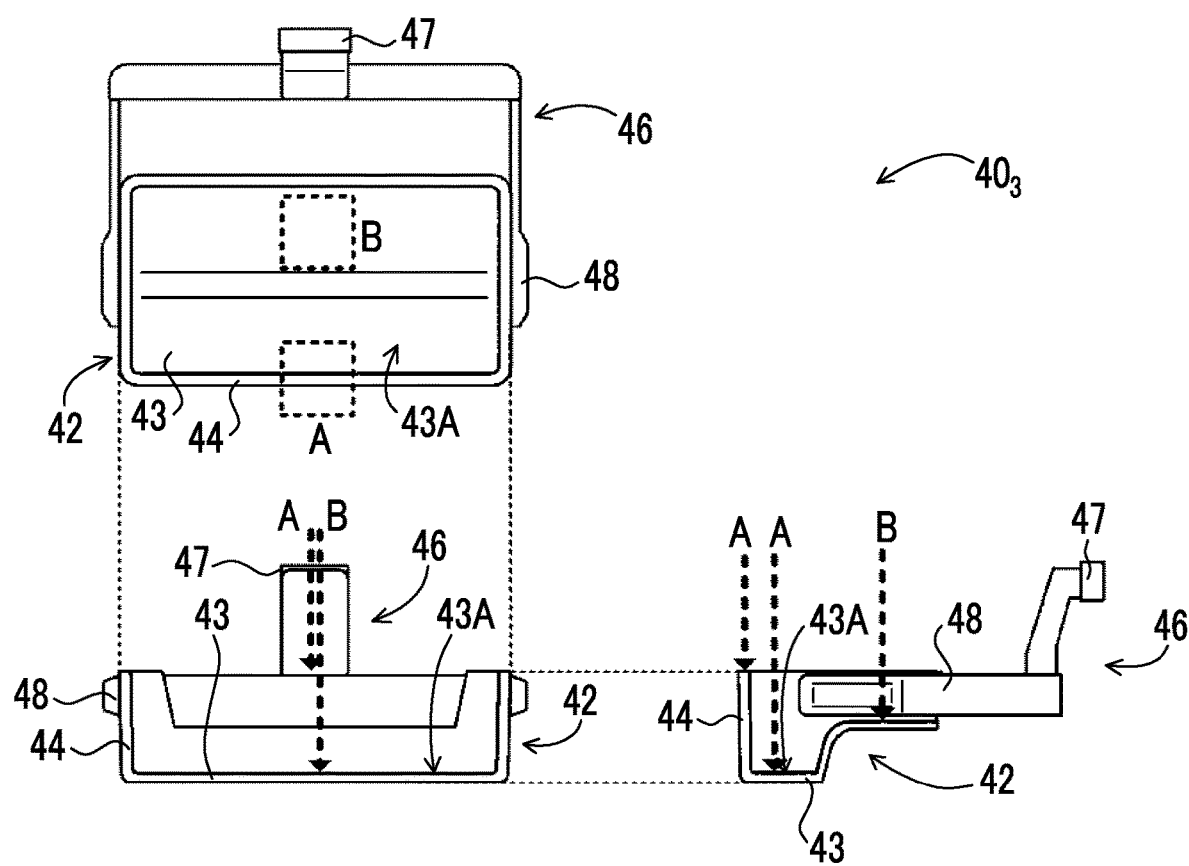
FIG. 12C is a three-view diagram illustrating still another example of the compression plate for explaining Modification Example 1.

In this modification example, as illustrated in FIGS. 12A to 12C, regions of the distance image 70 corresponding to regions A and B of the compression plate 40 are used for the above-described determination. Specifically, the regions of the distance image 70 (for convenience, referred to as a region A of the distance image 70 and a region B of the distance image 70) that correspond to the region A and the region B, respectively, in a state in which each compression plate 40 is attached to the mammography apparatus 10 are used for the above-described determination.

For example, in a case in which the distance indicated by a pixel group of a portion corresponding to the wall portion 44 of the region A which is obtained from the distance image 70 is equal to or less than a first threshold value, the determination unit 64 according to this modification example determines that the wall portion 44 is higher than that in the other compression plates 40 and the compression plate $40_1$ is attached. On the other hand, in a case in which the distance indicated by the pixel group of the portion corresponding to the wall portion 44 of the region A which is obtained from the distance image 70 is equal to or less than a second threshold value greater than the first threshold value, the determination unit 64 determines that the compression plate $40_2$ or the compression plate $40_3$ is attached. In addition, in a case in which the distance indicated by the pixel group of the portion corresponding to the wall portion 44 of the region A which is obtained from the distance image 70 is greater than the second threshold value, the determination unit 64 determines that the compression plate 40 is not attached to the mammography apparatus 10. The first threshold value is a threshold value for distinguishing the height of the wall portion 44 of the compression plate $40_1$ from the height of the wall portions 44 of the compression plates $40_2$ and $40_3$. The second threshold value is a threshold value for distinguishing the height of the wall portions 44 of the compression plates $40_2$ and $40_3$ from a state in which the compression plate 40 is not attached to the mammography apparatus 10. Therefore, the first threshold value and the second threshold value used for the determination are stored as the reference distance information 53 in the storage unit 52 in advance.

In addition, a determination method in the determination unit 64 is not limited to the above-described example. For example, for each type of the compression plate 40, information of the regions A and B of the distance image 70 captured by the TOF camera 39 in a state in which the compression plate 40 is attached to the initial position of the mammography apparatus 10 may be compared as the reference distance information 53 with each of the regions A and B of the distance image 70. Furthermore, for example, since the region A includes both the wall portion 44 and the bottom portion 43, a value corresponding to the distance between the wall portion 44 in the region A and the TOF camera 39 and a value corresponding the distance between the bottom portion 43 and the TOF camera 39 may be used as the reference distance information 53 for the region A. Since the region B includes the bottom portion 43, a value corresponding to the distance between the bottom portion 43 in the region B and the TOF camera 39 may be used as the reference distance information 53 for the region B.

Figure 13:
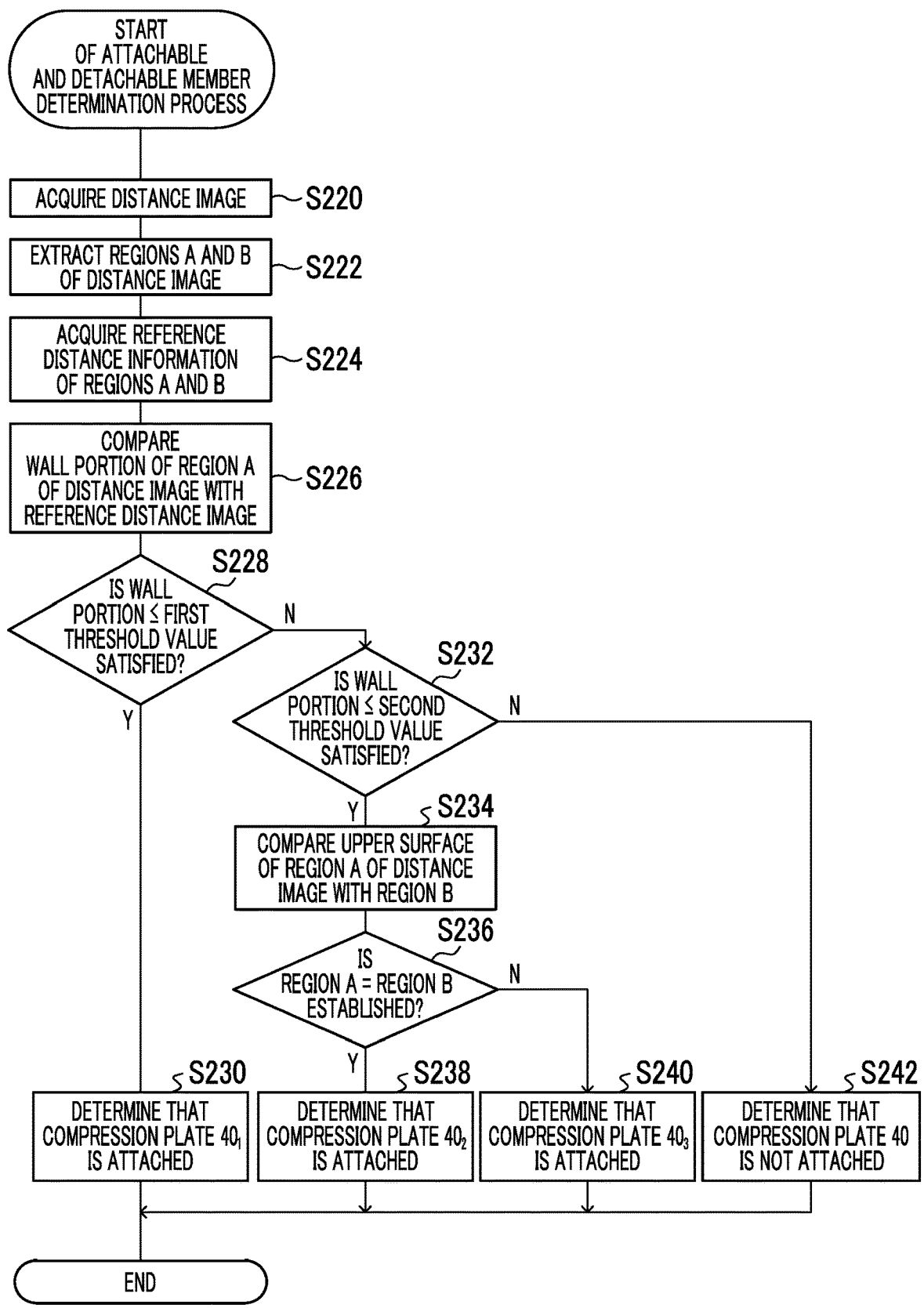
FIG. 13 is a flowchart illustrating an example of the flow of an attachable and detachable member determination process performed in information processing according to Modification Example 1.

Next, the operation of the console 12 according to this modification example will be described. In the information processing performed by the console 12 according to this modification example, since an attachable and detachable member determination process in Step S100 is different from the above-described attachable and detachable member determination process (see FIG. 7), the attachable and detachable member determination process according to this modification example will be described. FIG. 13 is a flowchart illustrating an example of the flow of the attachable and detachable member determination process according to this modification example.

In Step S220 of FIG. 13, the first acquisition unit 60 acquires the distance image 70 from the TOF camera 39 of the mammography apparatus 10 as in Step S200 of the attachable and detachable member determination process (see FIG. 7).

Then, in Step S222, the determination unit 64 extracts the region A and the region B from the distance image 70. For example, in this modification example, since information indicating the position of each of the region A and the region B of the distance image 70 is stored in the storage unit 52, the determination unit 64 extracts the region A and the region B from the distance image 70 on the basis of the information.

Then, in Step S224, the second acquisition unit 62 acquires the reference distance information 53 of each of the region A and the region B from the storage unit 52.

Then, in Step S226, the determination unit 64 compares a portion corresponding to the wall portion 44 of the region A of the distance image 70 with a portion corresponding to the wall portion 44 of the reference distance map 53A of the region A. Then, in Step S228, the determination unit 64 determines whether or not the distance indicated by a pixel group of a portion corresponding to the wall portion 44 of the region A of the distance image 70 is equal to or less than the first threshold value. In a case in which the distance indicated by the pixel group of the portion corresponding to the wall portion 44 of the region A of the distance image 70 is equal to or less than the first threshold value, the determination result in Step S228 is "Yes", and the process proceeds to Step S230. In Step S230, the determination unit 64 determines that the compression plate $40_1$ is attached to the mammography apparatus 10. In the compression plate $40_k$, the height of the wall portion 44 in the region A is the largest, and the distance between the TOF camera 39 and the compression plate $40_1$ is the shortest. Therefore, in a case in which the distance between the TOF camera 39 and the compression plate $40_1$ is equal to or less than the first threshold value, the determination unit 64 can determine that the compression plate $40_1$ is attached.

On the other hand, in a case in which the distance indicated by the pixel group of the portion corresponding to the wall portion 44 of the region A of the distance image 70 is not equal to or less than the first threshold value, the determination result in Step S228 is "No", and the process proceeds to Step S232. In Step S232, the determination unit 64 determines whether or not the distance indicated by the pixel group of the portion corresponding to the wall portion 44 of the region A of the distance image 70 is equal to or less than the second threshold value. In a case in which the distance indicated by the pixel group of the portion corresponding to the wall portion 44 of the region A of the distance image 70 is equal to or less than the second threshold value, the determination result in Step S232 is "Yes", and the process proceeds to Step S234.

In Step S234, the determination unit 64 compares the distance (hereinafter, referred to as a distance to the bottom portion 43 of the region A) indicated by a pixel group of a portion corresponding to the bottom portion 43 of the region A of the distance image 70 with the distance (hereinafter, referred to as a distance to the bottom portion 43 of the region B) indicated by a pixel group of a portion corresponding to the bottom portion 43 of the region B of the distance image 70. In the compression plate $40_2$ and the compression plate $40_3$, the wall portions 44 have a small height and have the same height in the region A in this modification example. Therefore, it is difficult to distinguish the compression plate $40_2$ and the compression plate $40_3$ on the basis of the height of the wall portion 44 in the region A. However, in the compression plate $40_2$, the height of the bottom portion 43 in the region A and the height of the bottom portion 43 in the region B are regarded as being equal to each other. In the compression plate $40_3$, the height of the bottom portion 43 in the region A and the height of the bottom portion 43 in the region B are different from each other. The bottom portion 43 in the region B is at a high position and the distance thereof from the TOP camera 39 is short. Therefore, in this modification example, for example, the distance to the bottom portion 43 of the region A of the distance image 70 is compared with the distance to the bottom portion 43 of the region B of the distance image 70 to determine whether the compression plate 40 attached to the mammography apparatus 10 is the compression plate $40_2$ or the compression plate $40_3$.

Then, in Step S236, the determination unit 64 determines whether or not the distance to the bottom portion 43 of the region A of the distance image 70 is equal to the distance to the bottom portion 43 of the region B of the distance image 70. In this determination, the determination that the distances are equal to each other is not limited to a case in which the distances are exactly equal to each other. For example, the distances may be determined to be equal to each other in consideration of errors. In a case in which the distance to the bottom portion 43 of the region A of the distance image 70 is equal to the distance to the bottom portion 43 of the region B of the distance image 70, the determination result in Step S236 is "Yes", and the process proceeds to Step S238. In Step S238, the determination unit 64 determines that the compression plate $40_2$ is attached to the mammography apparatus 10. As such, in a case in which the distance is equal to or less than the second threshold value greater than the first threshold value and the distance between the bottom portion 43 of the region A and the TOF camera 39 is equal to the distance between the bottom portion 43 of the region B and the TOF camera 39, it can be determined that the compression plate $40_2$ is attached.

On the other hand, in a case in which the distance to the bottom portion 43 of the region A of the distance image 70 is not equal to the distance to the bottom portion 43 of the region B of the distance image 70, the determination result in Step S236 is "No", and the process proceeds to Step S240.

In Step S240, the determination unit 64 determines that the compression plate $40_3$ is attached to the mammography apparatus 10. As such, in a case in which the distance is equal to or less than the second threshold value greater than the first threshold value and the distance between the bottom portion 43 of the region A and the TOF camera 39 is not equal to the distance between the bottom portion 43 of the region B and the TOF camera 39, it can be determined that the compression plate $40_3$ is attached.

Further, in Step S232, in a case in which the distance indicated by the pixel group of the portion corresponding to the wall portion 44 of the region A of the distance image 70 is not equal to or less than the second threshold value, the determination result in Step S232 is "No", and the process proceeds to Step S242. In Step S242, the determination unit 64 determines that the compression plate 40 is not attached to the mammography apparatus 10. As such, in a case in which the distance is greater than the second threshold value, it can be determined that the compression plate 40 is not attached to the mammography apparatus 10.

In a case in which any of the processes in Steps S230, S238, S240, and S242 ends, the attachable and detachable member determination process according to this modification example illustrated in FIG. 13 ends.

As such, in this modification example, the use of the distance image 70 and the reference distance information 53 makes it possible to determine whether or not the compression plate 40 is attached to the mammography apparatus 10 and to determine the type of the compression plate 40 in a case in which the compression plate 40 is attached.

Modification Example 2

In this modification example, a modification example of the reference distance information 53 will be further described.

In a case in which the compression plate 40 is provided with a convex or concave mark for identifying each type, the type of the compression plate 40 can be determined on the basis of the distance from the TOF camera 39 to the mark provided in the compression plate 40 or the shape of the mark.

Figure 14A:
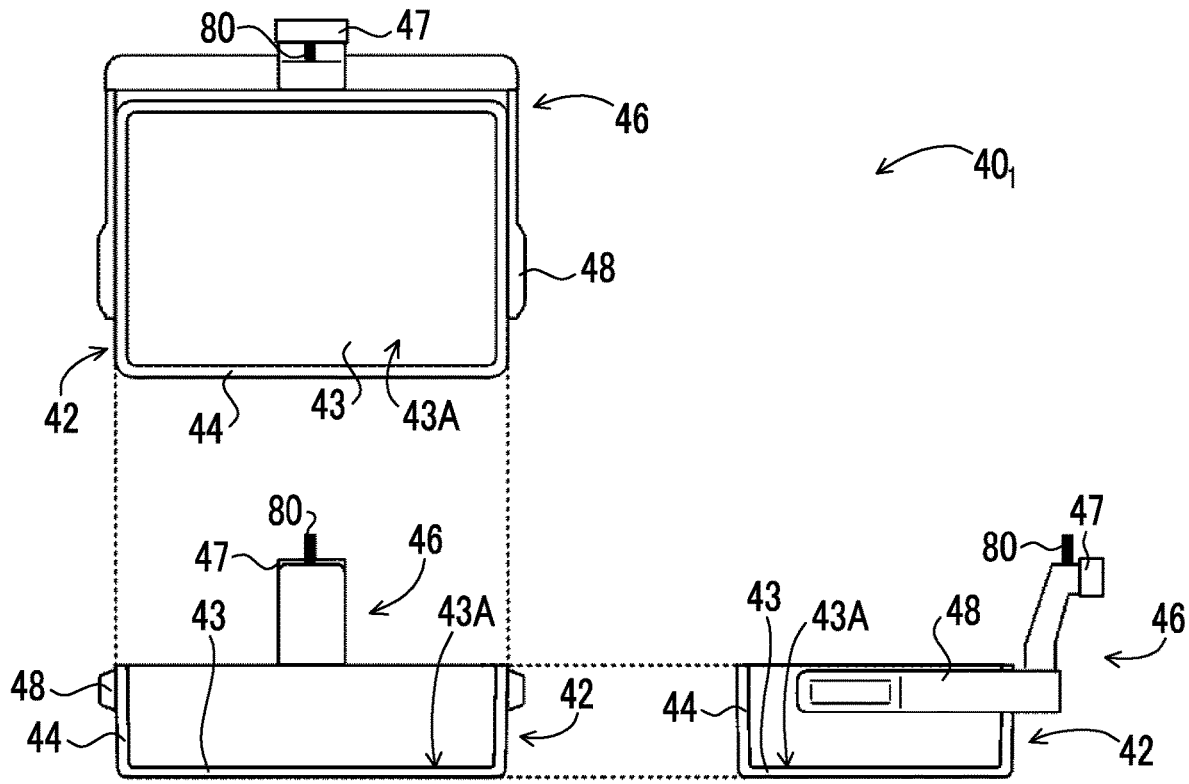
FIG. 14A is a three-view diagram illustrating an example of a compression plate for explaining Modification Example 2.
Figure 14B:
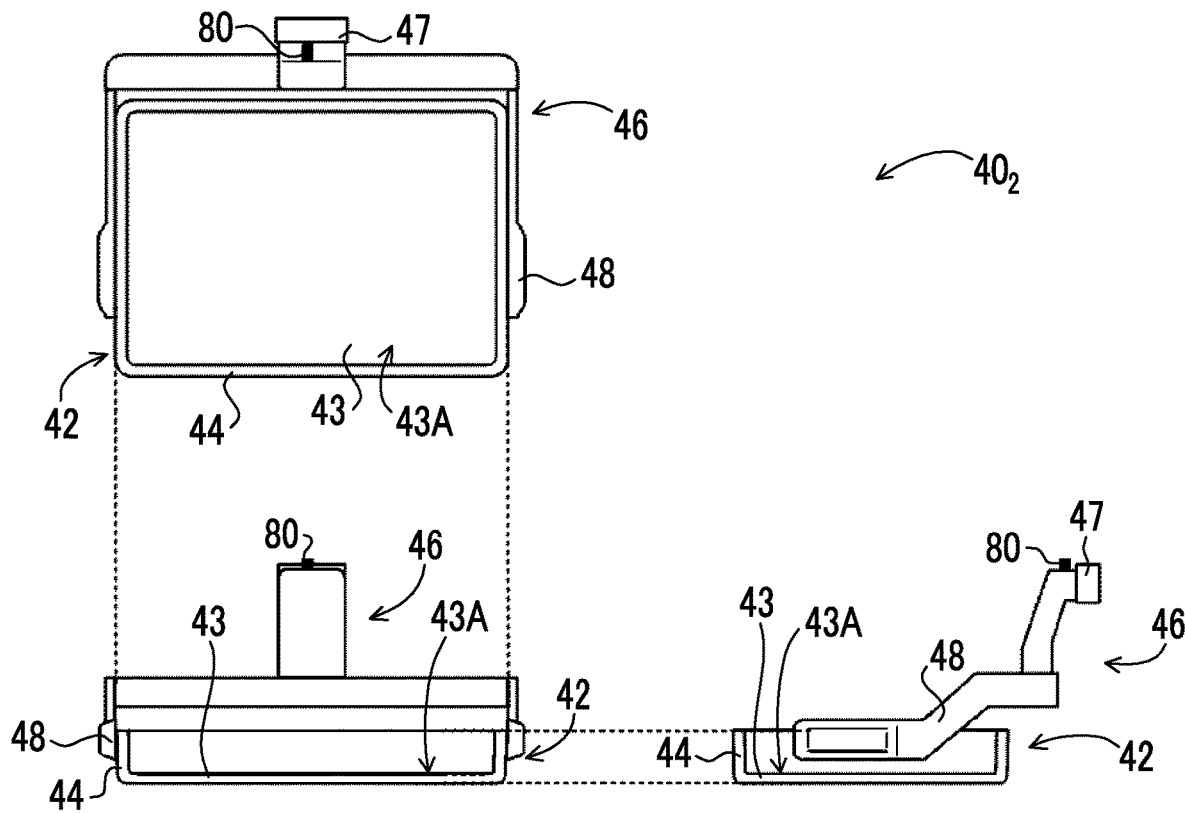
FIG. 14B is a three-view diagram illustrating another example of the compression plate for explaining Modification Example 2.

For example, FIGS. 14A and 14B illustrate an example in which a mark 80 for identifying the type of the compression plate 40 on the basis of the distance from the TOF camera 39 to the mark provided in the compression plate 40 is provided. As illustrated in FIGS. 14A and 14B, the mark 80 that is formed in a convex shape, specifically, protrudes in a direction in which it becomes closer to the TOF camera 39 is provided in the attachment portion 47 of the compression plate 40. The height of the mark 80 of the compression plate $40_1$ is larger than the height of the mark 80 of the compression plate $40_2$. That is, the distance between the TOF camera 39 and the mark 80 of the compression plate $40_1$ is shorter than the distance between the TOF camera 39 and the mark 80 of the compression plate $40_2$. In this case, for example, the distance between the mark 80 and the TOF camera 39 in a state in which the compression plate $40_1$ is attached to the initial position of the mammography apparatus 10 and the distance between the mark 80 and the TOF camera 39 in a state in which the compression plate $40_2$ is attached to the initial position of the mammography apparatus 10 can be applied as the reference distance information 53. In this aspect, information in which the reference distance information 53 and the type of the compression plate 40 are associated with each other may be obtained in advance.

Figure 15A:
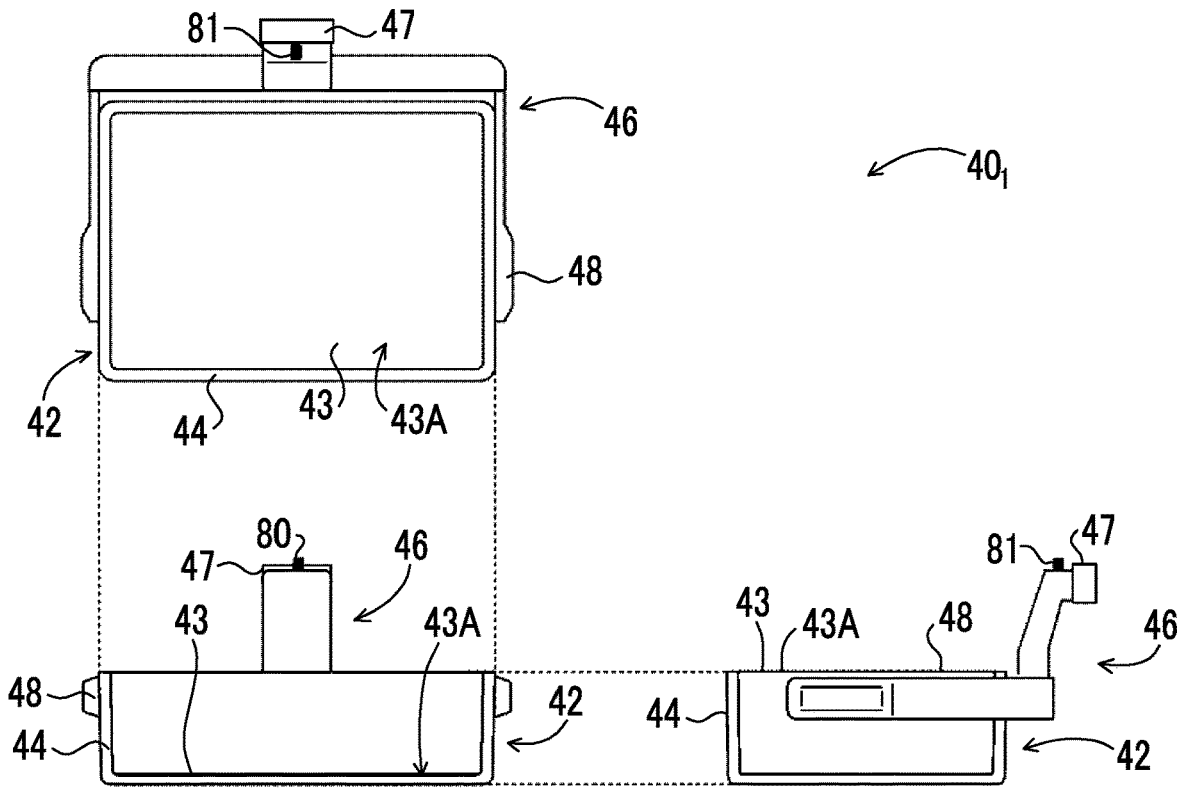
FIG. 15A is a three-view diagram illustrating an example of a compression plate for explaining Modification Example 2.
Figure 15B:
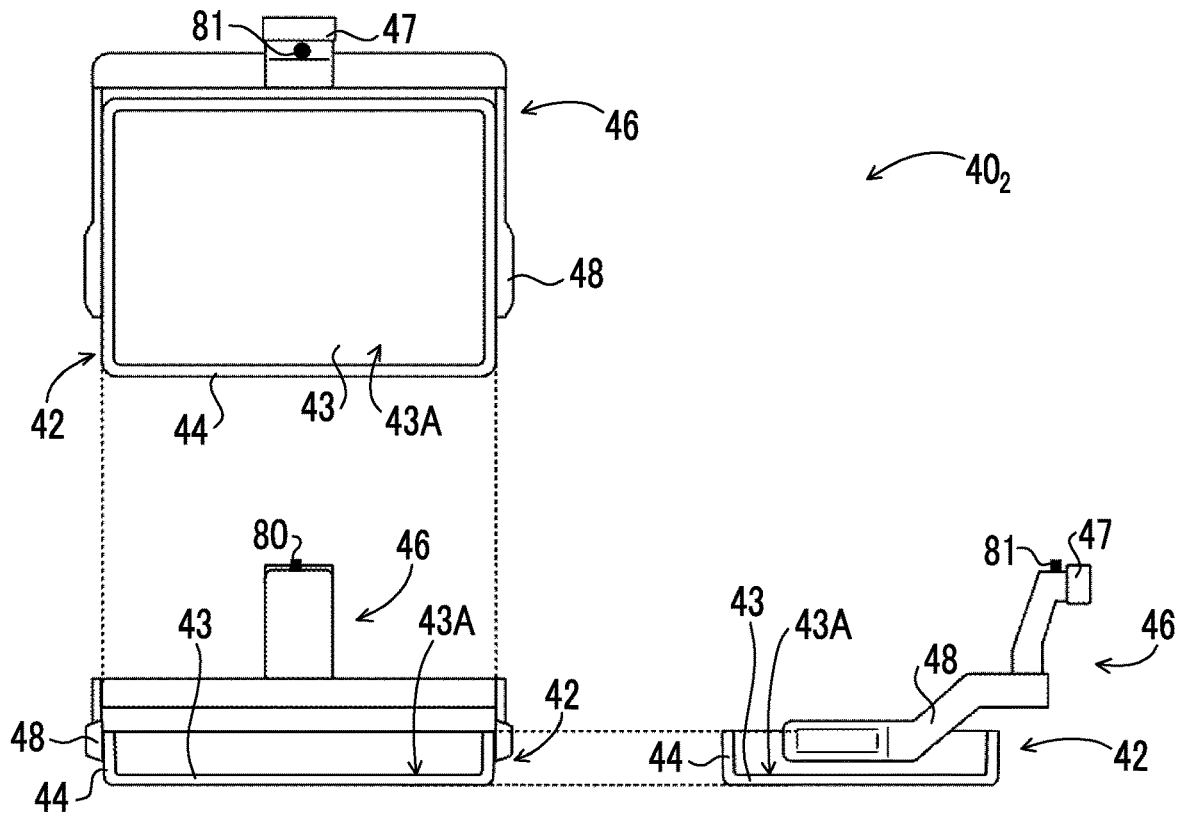
FIG. 15B is a three-view diagram illustrating another example of the compression plate for explaining Modification Example 2.

Further, for example, FIGS. 15A and 15B illustrate an example in which a mark 81 for identifying the type of the compression plate 40 on the basis of the shape is provided. As illustrated in FIGS. 15A and 15B, the mark 81 that is formed in a convex shape, specifically, protrudes in a direction in which it becomes closer to the TOF camera 39 is provided in the attachment portion 47 of the compression plate 40. The mark 81 of the compression plate $40_1$ has a prismatic shape, and the shape of the mark 81 in the distance image 70 is a rectangle. In contrast, the mark 81 of the compression plate $40_2$ has a cylindrical shape, and the shape of the mark 81 in the distance image 70 is a circle. In this case, for example, the shape of each mark 81 and the distance between the mark 81 and the TOF camera 39 in a state in which the compression plate 40 is attached to the initial position of the mammography apparatus 10 can be applied as the reference distance information 53.

In addition, in a case in which the height of the prismatic mark 81 of the compression plate $40_1$ is equal to the height of the cylindrical mark 81 of the compression plate $40_2$, the reference distance information 53 is the same. However, for the prismatic mark 81 of the compression plate $40_1$ and the cylindrical mark 81 of the compression plate $40_2$, the shapes of the images corresponding to the marks 81 in the distance image 70 are different from each other. Therefore, information in which the shape of the image corresponding to the mark 81 in the distance image 70 and the type of the compression plate 40 are associated with each other is obtained in advance. For example, the determination unit 64 may perform image analysis for determining the shape of the image corresponding to the mark 81 on the distance image 70 and may specify the type of the compression plate 40 which corresponds to the image corresponding to the determined mark 81 to determine the type of the compression plate 40 attached to the mammography apparatus 10. In addition to the marks 81 illustrated in FIGS. 15A and 15B, for example, letters or identification symbols indicating the identification (ID) of the compression plate 40 may be used as the marks 81.

As described above, the console 12 according to each of the above-described aspects comprises the CPU 50A as at least one processor and the ROM 50B storing the commands that can be executed by the CPU 50A. The CPU 50A acquires the distance image 70 which indicates the distance to an imaging target and is captured by the TOF camera 39 using, as an imaging region, a region including at least a portion of the region in which the attachable and detachable member is attached to the mammography apparatus 10. Further, the CPU 50A acquires the reference distance information 53 related to the reference value of the distance between the attachable and detachable member and the TOF camera 39 in a state in which the attachable and detachable member is attached to the mammography apparatus 10. Furthermore, the CPU 50A determines whether or not the attachable and detachable member is attached to the mammography apparatus 10 on the basis of the distance image and the reference distance information 53.

As the related art different from the present disclosure, for example, there is an aspect in which identification information for identifying the type of the compression plate is provided on the compression plate and an identification sensor provided in a mammography apparatus main body reads the identification information to identify the type of the compression plate. In this aspect, in a case in which there are many types of compression plates or in a case in which the types of compression plates are newly increased, it may be difficult for the current sensor to respond to the case, or the size of the apparatus may increase.

In contrast, the console 12 according to the present disclosure can determine whether or not the compression plate 40 is attached from the distance image 70 captured by the TOF camera 39 and the reference distance information 53 and can also determine the type of the compression plate 40 in a case in which the compression plate 40 is attached. Therefore, the console 12 according to each of the above-described aspects can perform determination related to the attachable and detachable member attached to the mammography apparatus 10 with a simple configuration.

Further, in each of the above-described aspects, the aspect in which the reference distance map 53A is used as an example of the reference distance information 53 has been described. However, the reference distance information 53 is not limited to the reference distance map 53A. As described above, the reference distance information 53 may be information related to the reference value of the distance between the attachable and detachable member and the TOF camera 39 in a case in which the attachable and detachable member, such as the compression plate 40, is attached to the mammography apparatus 10. For example, a design value in a case in which the attachable and detachable member is attached to the mammography apparatus 10 may be used as the reference value. In this case, information indicating the design value is the reference distance information 53. Further, in this case, for example, the position of a region of an image indicating the attachable and detachable member in the distance image 70 may be determined in advance, and the determination unit 64 may perform the attachable and detachable member determination process (see FIG. 7 and the like) on the basis of the distance indicated by the image of the region and the reference distance information 53.

In each of the above-described aspects, the compression plate 40 has been described as an example of the attachable and detachable member according to the present disclosure. However, the attachable and detachable member according to the present disclosure is not limited to the compression plate 40. For example, the face guard 38 is an example of the attachable and detachable member according to the present disclosure and is also an example of the protective member according to the present disclosure. The face guard 38 and the compression plate 40 are attached to the mammography apparatus 10 at different positions. In this configuration, in a case in which the TOF camera 39 captures one distance image 70 using the face guard 38 and the compression plate 40 as the imaging target, each of a region including the face guard 38 and a region including the compression plate 40 is obtained. Therefore, on the basis of one distance image 70, it is possible to determine whether or not a plurality of attachable and detachable members are attached and to determine the types of the attachable and detachable members in a case in which the attachable and detachable members are attached. As such, the console 12 according to this aspect can perform determination for a plurality of attachable and detachable members on the basis of one distance image 70. Therefore, it is possible to perform determination related to the attachable and detachable member attached to the mammography apparatus 10 with a simpler configuration. In addition, other examples of the attachable and detachable member include a magnification imaging table and a biopsy unit.

In addition, in each of the above-described aspects, as an example of the aspect of capturing the distance image, the aspect has been described in which the TOF camera is used to capture the distance image using the TOF method. However, the imaging device for capturing the distance image is not limited to the TOF camera. For example, the following aspect may be used: an imaging device that irradiates an imaging target with infrared light having a pattern and captures a distance image corresponding to reflected light from the imaging target is used, and a structured light method is applied to capture the distance image. Further, for example, a depth-from-defocus (DFD) method that restores the distance on the basis of the degree of blurring of an edge region in the distance image may be applied. In the case of this aspect, for example, an aspect is known which uses a distance image captured by a monocular camera using a color aperture filter.

In addition, in each of the above-described aspects, the aspect has been described in which the TOF camera 39 is provided on the side close to the compression unit 36 in the radiation emitting unit 37 of the mammography apparatus 10. However, the position where the TOF camera 39 is provided is not limited to this aspect. The TOF camera 39 may be disposed at a position where it can capture the image of at least a portion of the region in which the attachable and detachable member is attached to the mammography apparatus 10, specifically, a region including a portion in which it can be determined whether or not the attachable and detachable member is attached. However, the position of the TOF camera 39 is not limited. For example, the TOF camera 39 may be provided on the side close to the face guard 38 in the radiation emitting unit 37. Further, for example, the TOF camera 39 may be provided outside the mammography apparatus 10.

Further, in each of the above-described aspects, the aspect has been described in which the mammography apparatus 10 is applied as an example of the radiography apparatus according to the present disclosure. However, the radiography apparatus is not limited to the mammography apparatus. For example, a radiography apparatus for performing general imaging may be applied.

Further, in each of the above-described aspects, the aspect has been described in which the console 12 is an example of the information processing apparatus according to the present disclosure. However, apparatuses other than the console 12 may have the functions of the information processing apparatus according to the present disclosure. In other words, for example, the mammography apparatus 10 or an external apparatus other than the console 12 may have some or all of the functions of the first acquisition unit 60, the second acquisition unit 62, and the determination unit 64.

Further, in each of the above-described aspects, for example, the following various processors can be used as the hardware structure of processing units performing various processes such as the first acquisition unit 60, the second acquisition unit 62, and the determination unit 64. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the information processing program 51 is stored (installed) in the storage unit 52 in advance has been described. However, the invention is not limited thereto. The information processing program 51 may be recorded on a recording medium, such as a compact disc read only memory (CD-ROM), a digital versatile disc read only memory (DVD-ROM), or a universal serial bus (USB) memory, and then provided. In addition, the information processing program 51 may be downloaded from an external apparatus through the network.

What is claimed is:

1. An information processing apparatus comprising:
   at least one processor; and
   a memory that stores commands executable by the processor,
   wherein the processor acquires a distance image which indicates a distance to an imaging target and is captured by an imaging device using, as an imaging region, a region including at least a portion of a region in which an attachable and detachable member is attached to a radiography apparatus, acquires reference distance information related to a reference value of a distance between the attachable and detachable member and the imaging device in a state in which the attachable and detachable member is attached to the radiography apparatus, and determines whether or not the attachable and detachable member is attached to the radiography apparatus on the basis of the distance image and the reference distance information.

2. The information processing apparatus according to claim 1,
   wherein a plurality of types of the attachable and detachable members are provided, and
   the processor determines the type of the attachable and detachable member on the basis of the distance image and the reference distance information.

3. The information processing apparatus according to claim 2,
   wherein, in each type of the attachable and detachable member, at least one of a position where the attachable and detachable member is attached to the radiography apparatus or the distance between the attachable and detachable member and the imaging device in a state in which the attachable and detachable member is attached to the radiography apparatus is different.

4. The information processing apparatus according to claim 1,
   wherein the radiography apparatus is a mammography apparatus that captures an image of a breast of a subject, and
   the attachable and detachable member is at least one of a compression member that compresses the breast, a protective member that protects the subject from radiation, a magnification imaging table, or a biopsy unit.

5. The information processing apparatus according to claim 1,
   wherein the radiography apparatus is a mammography apparatus that captures an image of a breast of a subject,
   the attachable and detachable member includes at least a plurality of types of compression members that compress the breast, and
   the processor determines the type of the compression member attached to the radiography apparatus on the basis of the distance image and the reference distance information.

6. The information processing apparatus according to claim 5,
   wherein the plurality of types of compression members are provided with marks having different distances from the imaging device for each type.

7. The information processing apparatus according to claim 5,
   wherein the plurality of types of compression members are provided with convex or concave marks having different shapes for each type.

8. The information processing apparatus according to claim 1,
   wherein the reference distance information is a reference distance map indicating the distance between the imaging device and the attachable and detachable member attached to the radiography apparatus.

9. The information processing apparatus according to claim 1,
   wherein the imaging device captures the distance image using a time-of-flight (TOF) method.

10. An information processing method execute by a computer, the method comprising:
    acquiring a distance image which indicates a distance to an imaging target and is captured by an imaging device using, as an imaging region, a region including at least a portion of a region in which an attachable and detachable member is attached to a radiography apparatus;
    acquiring reference distance information related to a reference value of a distance between the attachable and detachable member and the imaging device in a state in which the attachable and detachable member is attached to the radiography apparatus; and
    determining whether or not the attachable and detachable member is attached to the radiography apparatus on the basis of the distance image and the reference distance information.

11. A non-transitory computer-readable storage medium storing an information processing program that causes a computer to perform a process comprising:
    acquiring a distance image which indicates a distance to an imaging target and is captured by an imaging device using, as an imaging region, a region including at least a portion of a region in which an attachable and detachable member is attached to a radiography apparatus;
    acquiring reference distance information related to a reference value of a distance between the attachable and detachable member and the imaging device in a state in which the attachable and detachable member is attached to the radiography apparatus; and
determining whether or not the attachable and detachable member is attached to the radiography apparatus on the basis of the distance image and the reference distance information.

\* \* \* \* \*